(12) United States Patent
Ziolo et al.

(10) Patent No.: US 8,998,963 B2
(45) Date of Patent: Apr. 7, 2015

(54) PLATE/SCREW LOCKING MECHANISM DEVICES, SYSTEMS AND METHODS

(75) Inventors: Tara Ziolo, Hewitt, NJ (US); Stephen Termyna, Boonton, NJ (US); John Lovell, North Bergen, NJ (US)

(73) Assignee: Blackstone Medical, Inc., Lewisville, TX (US)

( * ) Notice: Subject to any disclaimer, the term of this patent is extended or adjusted under 35 U.S.C. 154(b) by 0 days.

(21) Appl. No.: 13/341,729

(22) Filed: Dec. 30, 2011

(65) Prior Publication Data

US 2013/0172939 A1 Jul. 4, 2013

(51) Int. Cl.
*A61B 17/80* (2006.01)
*A61B 17/86* (2006.01)
*A61B 17/00* (2006.01)

(52) U.S. Cl.
CPC ......... *A61B 17/8038* (2013.01); *A61B 17/8605* (2013.01); *A61B 17/8685* (2013.01); *A61B 2017/00004* (2013.01)

(58) Field of Classification Search
CPC . A61B 17/80; A61B 17/7059; A61B 17/8052
USPC ............ 606/300–321, 280–299, 70, 71
See application file for complete search history.

(56) References Cited

U.S. PATENT DOCUMENTS

| | | | |
|---|---|---|---|
| 5,616,144 A * | 4/1997 | Yapp et al. | 606/280 |
| 2004/0127896 A1 | 7/2004 | Lombardo et al. | |
| 2005/0251137 A1 | 11/2005 | Ball | |
| 2006/0122604 A1 | 6/2006 | Gorhan et al. | |
| 2008/0177330 A1 * | 7/2008 | Ralph et al. | 606/290 |
| 2009/0064488 A1 | 3/2009 | Davies | |
| 2009/0192553 A1 * | 7/2009 | Maguire et al. | 606/305 |

OTHER PUBLICATIONS

International Search Report & Written Opinion, PCT/US2012/072112, dated Mar. 13, 2013, 8 pages.

* cited by examiner

*Primary Examiner* — Mary Hoffman
*Assistant Examiner* — Christina Negrellirodriguez
(74) *Attorney, Agent, or Firm* — Baker & McKenzie LLP

(57) ABSTRACT

The present disclosure relates, in some embodiments, to locking mechanisms for a fastener (e.g., a bone screw) and associated devices, systems, and methods. According to some embodiments, a lockable bone plate assembly may comprise, for example, a bone plate and a bone screw assembly. A bone plate may comprise, in some embodiments, at least one through hole, the at least one through hole having at least one bone plate hole circumferential recess. According to some embodiments, a bone screw assembly may comprise (a) a bone screw, (b) at least one deployable protrusion, and/or (c) a protrusion driver. The present disclosure further relates, in some embodiments, to methods for bone (e.g., vertebral) fixation. For example, a method may comprise contacting at least a portion of a spine (e.g., cervical spine) of a subject with a lockable bone plate assembly.

20 Claims, 24 Drawing Sheets

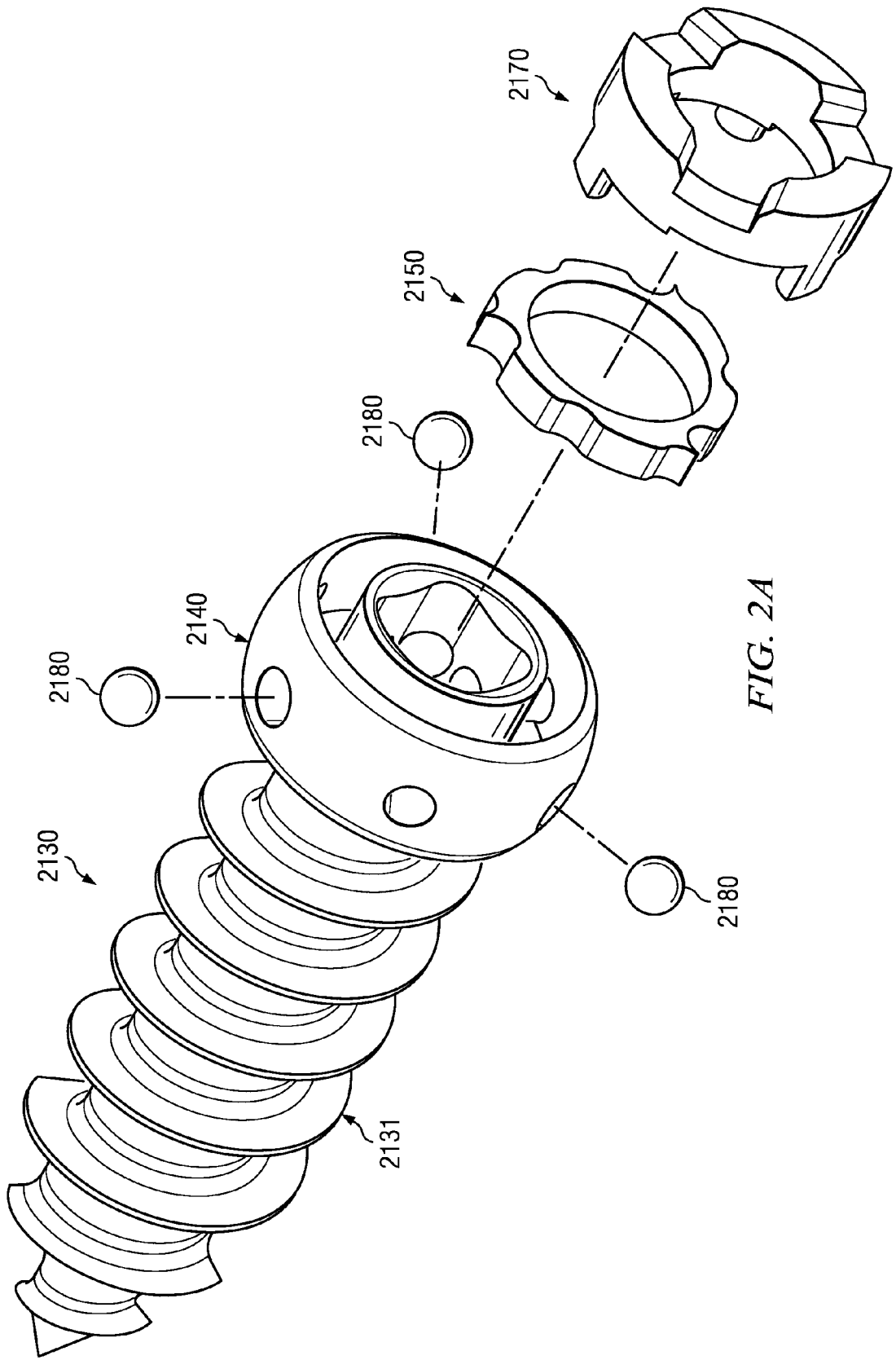

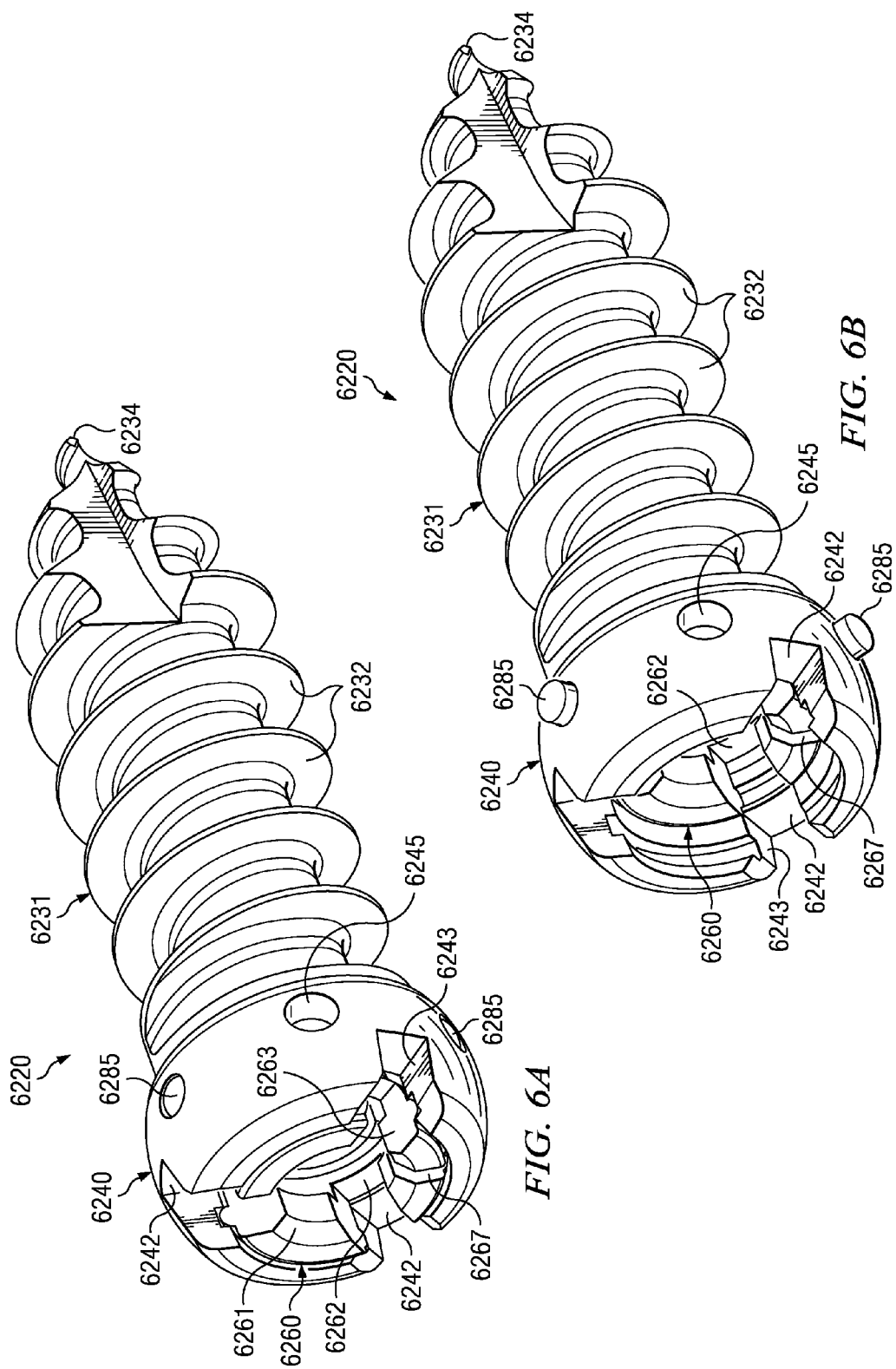

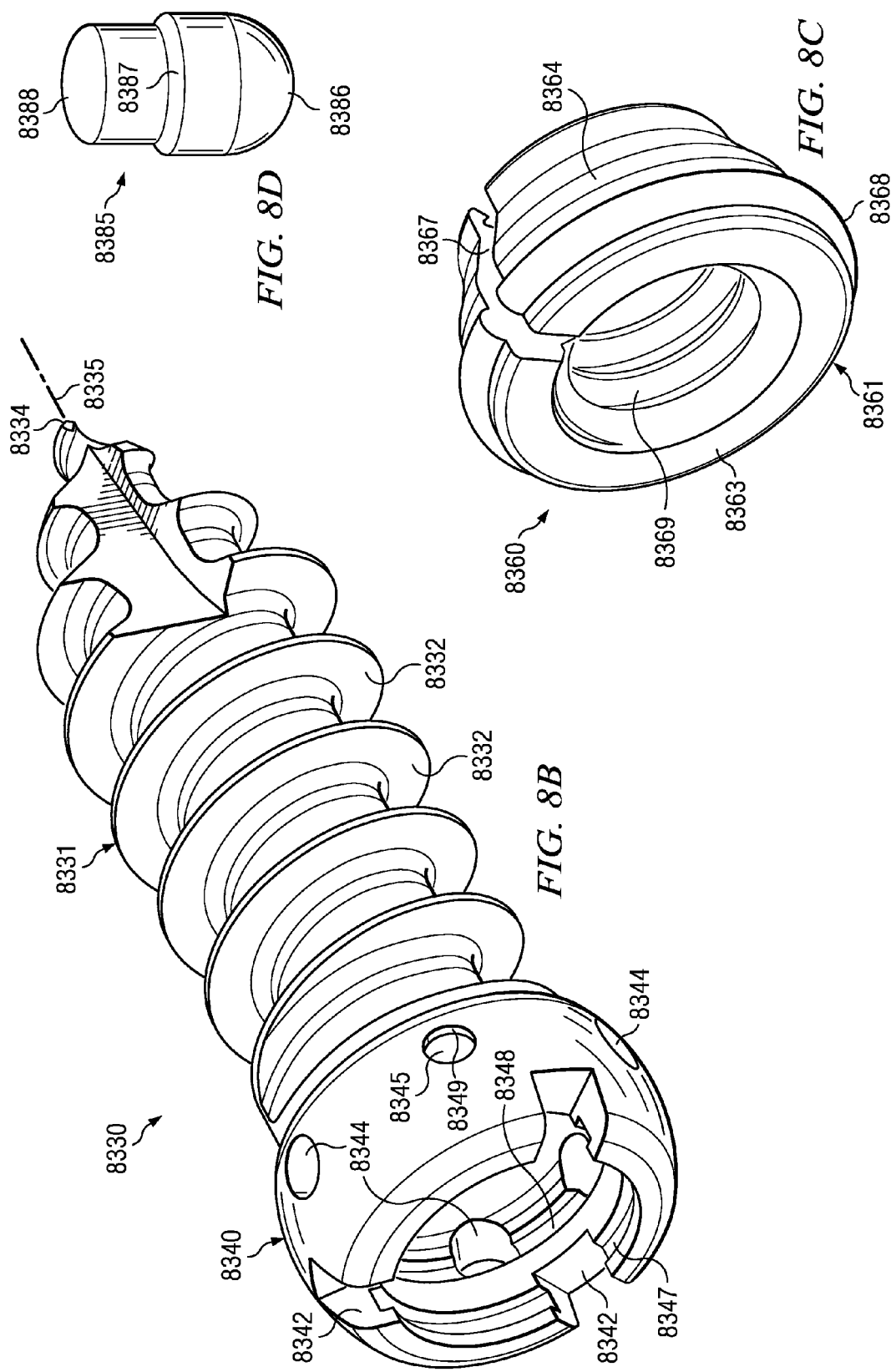

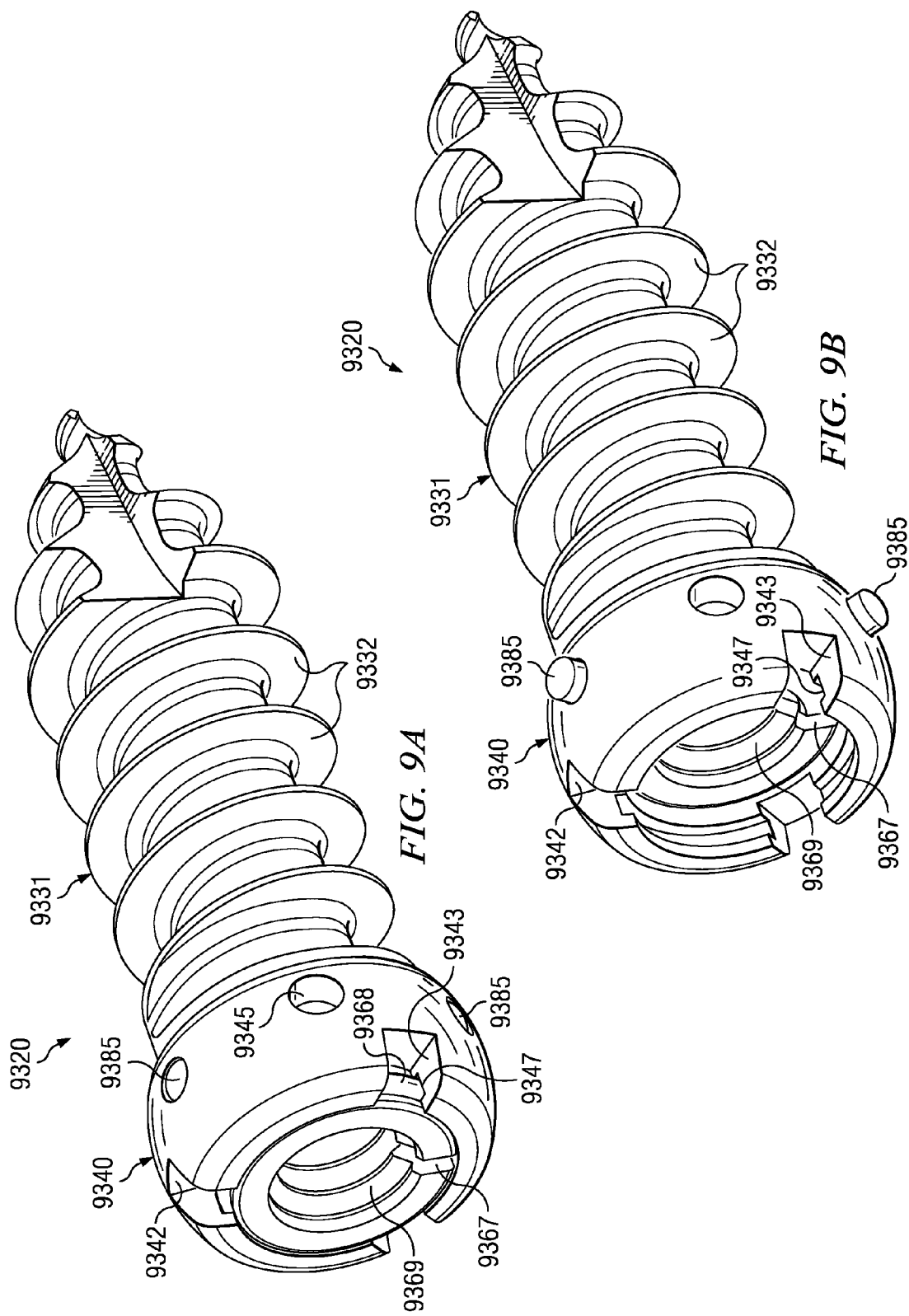

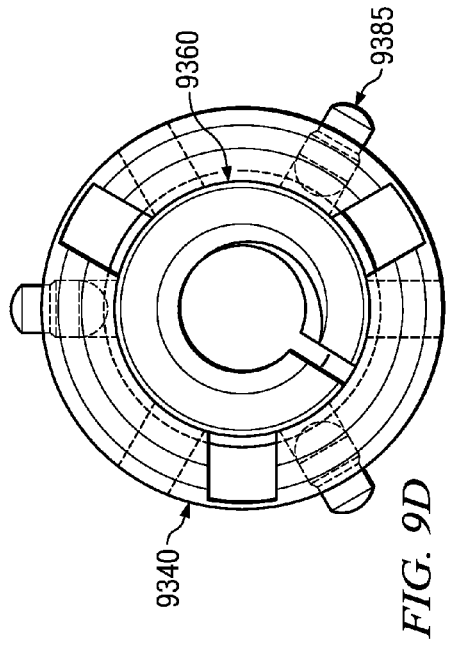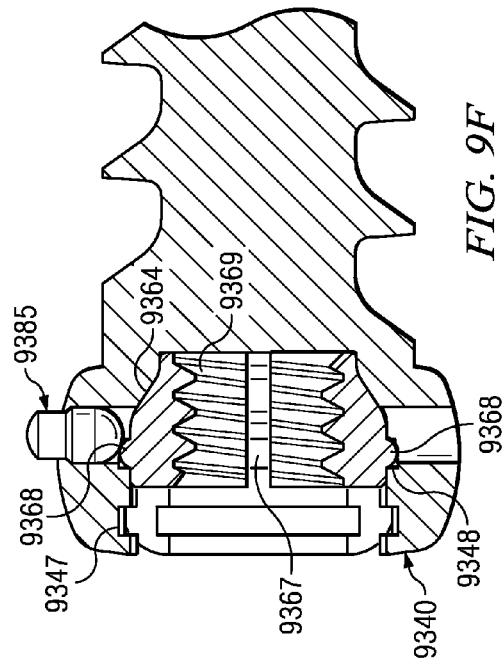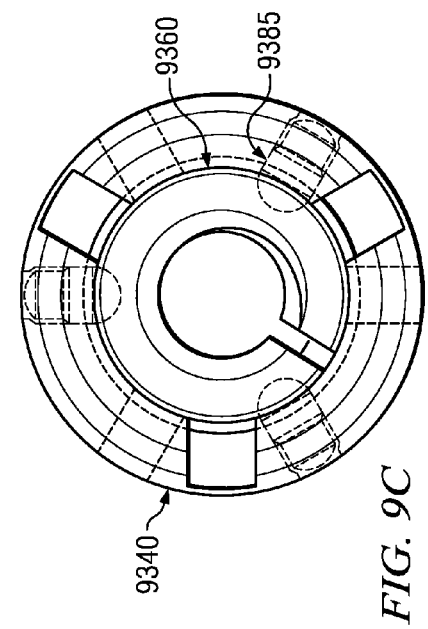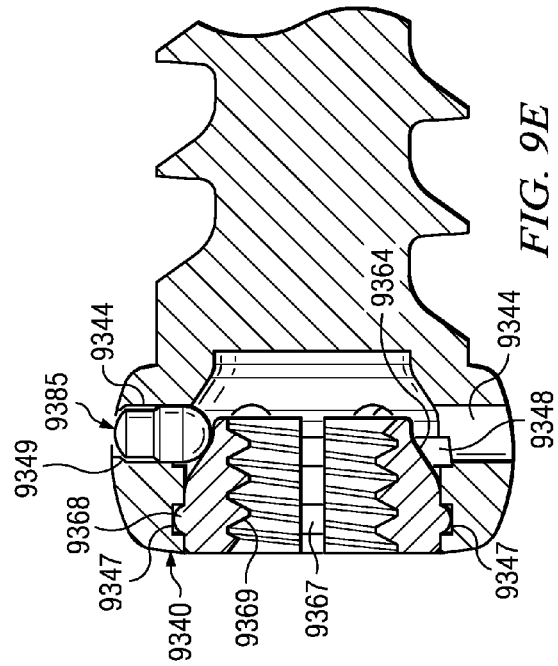

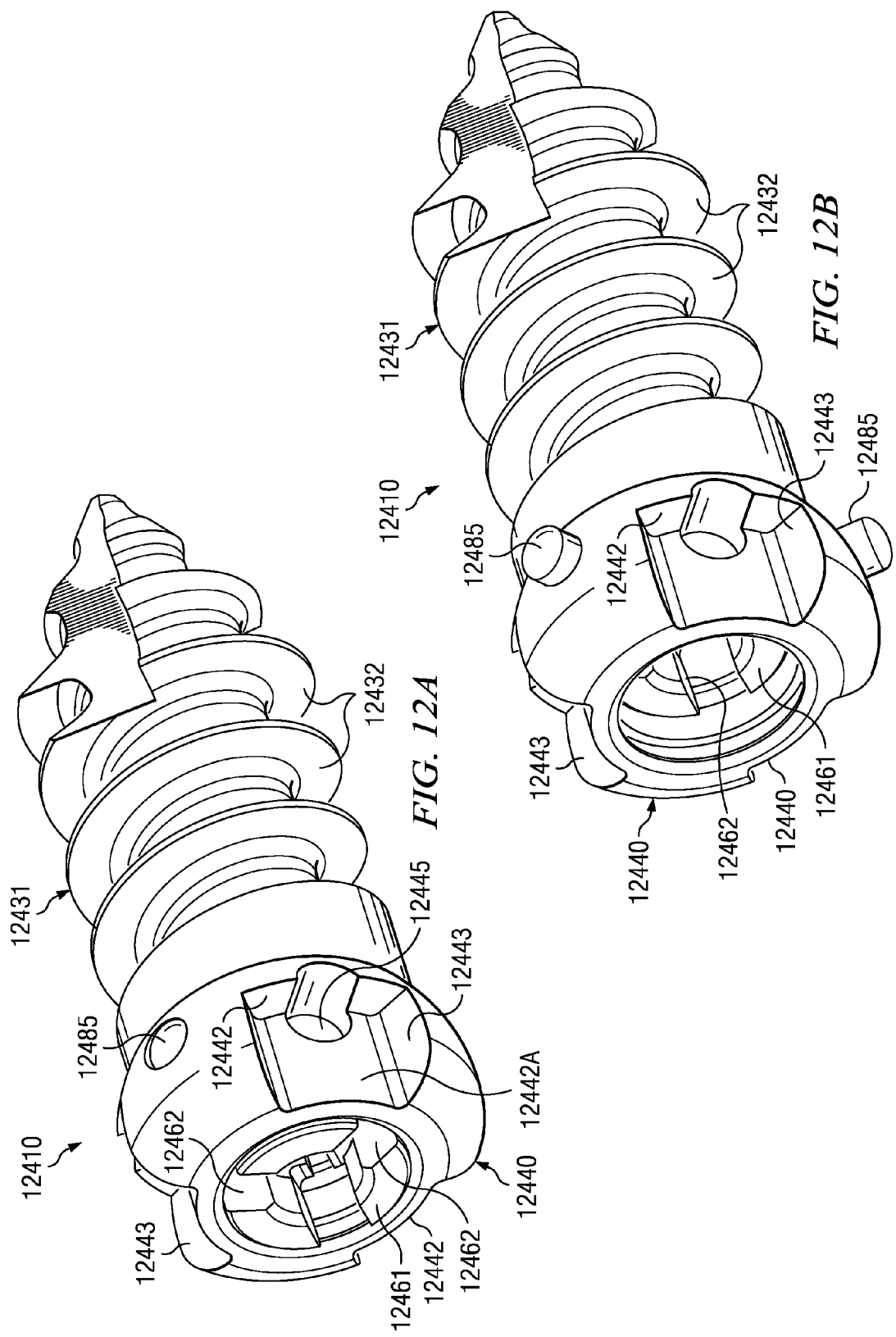

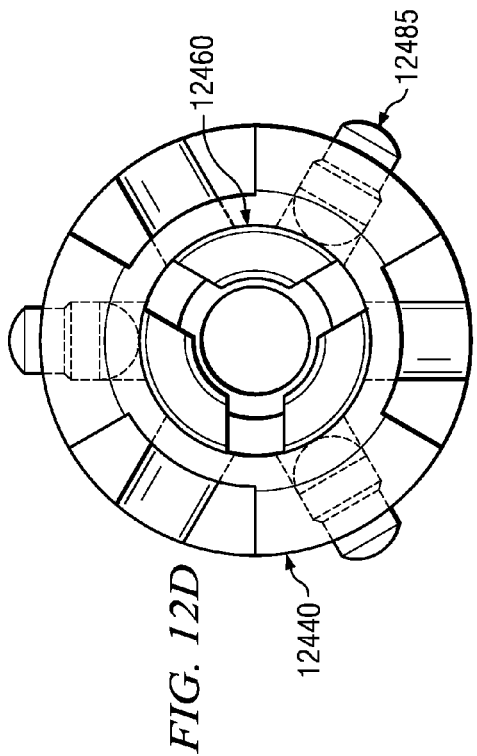
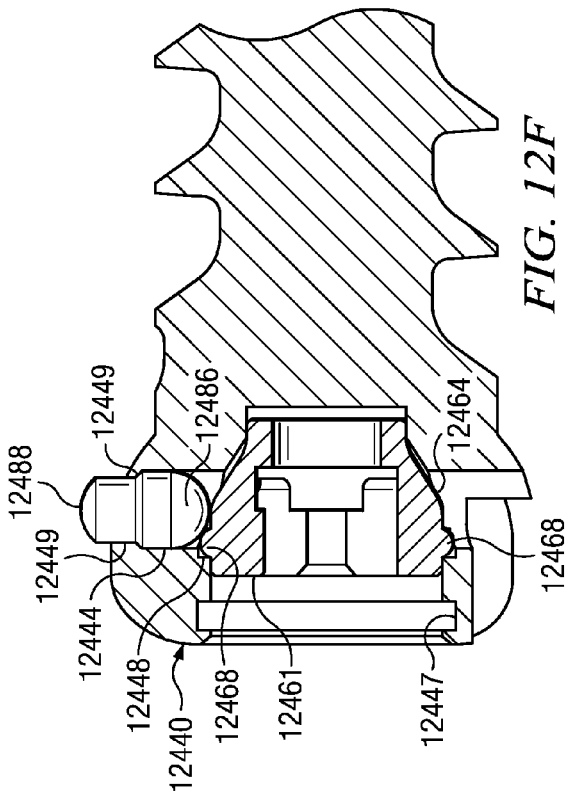
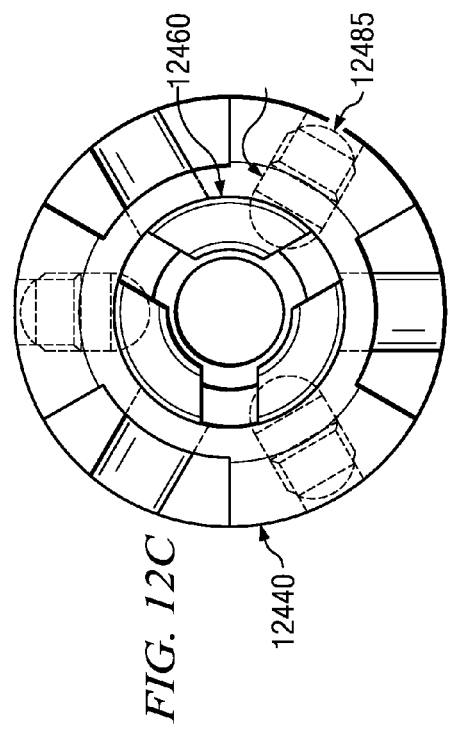
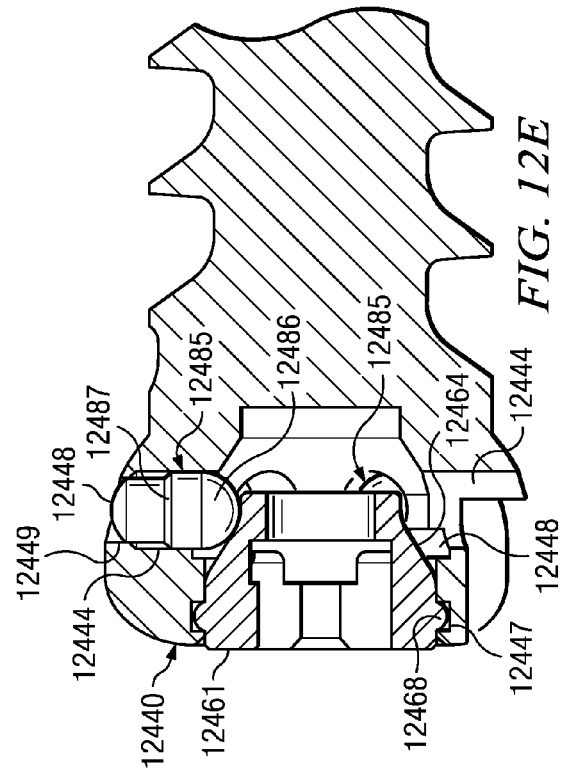

PLATE/SCREW LOCKING MECHANISM DEVICES, SYSTEMS AND METHODS

FIELD OF THE DISCLOSURE

The present disclosure relates, in some embodiments, to locking mechanisms for a fastener (e.g., a bone screw) and associated devices, systems, and methods.

BACKGROUND OF THE DISCLOSURE

The spinal column is a highly complex anatomical structure capable of bearing substantial loads while displaying remarkable flexibility. A variety of conditions (e.g., traumatic, pathological, developmental, and/or degenerative) exist that may impair the load bearing capacity, flexibility, or both of a subject's spine. Under such circumstances and others, it may be desirable to attach one or more appliances to a subject's spine using one or more fasteners (e.g., screws, clamps, clips, and/or other devices). A fastener (e.g., a screw) inserted into the spine may backout of the insertion site, for example, through the course of a subject's normal activities.

SUMMARY

Accordingly, a need has arisen for improved methods and mechanisms for securing a fastener (e.g., a bone screw). The present disclosure relates, in some embodiments, to locking mechanisms for a fastener (e.g., a bone screw) and associated devices, systems, and methods. According to some embodiments, a locking mechanism may reduce, arrest, and/or prevent backout of a fastener.

The present disclosure relates, in some embodiments, to a lockable bone plate assembly, which may comprise, for example, a bone plate and a bone screw assembly. A bone plate may comprise, in some embodiments, at least one through hole, the at least one through hole having at least one bone plate hole circumferential recess. According to some embodiments, a bone screw assembly may comprise (a) a bone screw, (b) at least one deployable protrusion, and/or (c) a protrusion driver. A deployable protrusion may have a stowed position (e.g., substantially within the bone screw) and/or a deployed position (e.g., at least partially protruding from the bone screw). In a deployed position, a deployable protrusion may engage a bone plate hole circumferential recess. According to some embodiments, a protrusion driver may be in mechanical communication with a deployable protrusion and operable to drive the deployable protrusion from a stowed position to a deployed position. A vertical position of a bone screw relative to a bone and/or a bone screw plate may be locked, in some embodiments, when a deployable protrusion is in a deployed position.

According to some embodiments, a protrusion driver may be configured to move a deployable protrusion radially outwardly from a stowed position to a deployed position. A protrusion driver and/or a deployable protrusion may have a stowed position and/or a deployed position. For example, a protrusion driver may have a deployed position corresponding to a deployed position of a deployable protrusion. A protrusion driver may be configured to be locked in a deployed position in some embodiments. For example, a bone screw may comprise a first surface feature (e.g., ridge, bump, nub, point, groove, slot, and/or the like) and a protrusion driver may comprise a second surface feature (e.g., ridge, bump, nub, point, groove, slot, and/or the like) configured to engage the first surface feature and lock the protrusion driver in its deployed position. According to some embodiments, a bone screw may comprise a central, longitudinal axis, a bone screw body, and/or a bone screw head. A bone screw head may, for example, comprise at least one notch (e.g., a centrally-located and/or top-facing notch). One or more (e.g., up to all) bone screw head notches may comprise a torque surface configured to receive a torque and translate the torque to rotation of the bone screw about the central, longitudinal axis (e.g., clockwise or counterclockwise). A bone screw body may comprise one or more threads that taper to a tip (e.g., the lengthwise end opposite a bone screw head). For example, a lockable bone plate assembly may comprise a bone screw having a central longitudinal axis and comprising a bone screw body comprising threads that taper to a tip and a bone screw head fixed to the bone screw body on the end opposite the tip, the bone screw head comprising at least one notch. According to some embodiments, a bone screw head may comprise a groove, for example, an annular groove. An annular groove may be positioned in a bone screw head also comprising a notch in some embodiments. For example, an annular groove may encircle a notch (e.g., a centrally-located and/or top-facing notch).

A bone screw assembly (e.g., comprised in a lockable bone plate assembly) may comprise an annular bone screw cam and/or an annular bone screw cap according to some embodiments. An annular bone screw cam may be positioned, for example, in an annular groove of a bone screw head. In some embodiments, an annular bone screw cam may comprise on its outer circumferential surface at least one axial groove, at least one axial deep recess, at least one axial shallow recess between the axial groove and the axial deep recess, and/or at least one cam surface. An annular bone screw cap may comprise, according to some embodiments, a first surface comprising at least one bone screw cap notch and second surface opposing the first facing the annular bone screw cam and comprising at least one prong. In some embodiments, a deep recess may be configured to engage a deployable protrusion in its stowed position a shallow recess may be configured to engage the deployable protrusion in its deployed position, and/or a axial groove may be in mechanical communication with a prong to produce tandem rotation of an annular bone screw cam and an annular bone screw cap about the central, longitudinal axis of the bone screw. An annular bone screw cap may comprise, according to some embodiments, at least one circumferential notch comprising a torque surface, the torque surface configured to receive a torque and translate the torque to rotation of the bone screw cap about the central, longitudinal axis.

A bone screw head may comprise a central cavity in some embodiments. A central cavity may comprise, for example, a central cavity inner surface, the inner surface comprising a stowed circumferential recess (e.g., defining a plane perpendicular to the central, longitudinal axis of the bone screw) and a deployed circumferential recess (e.g., defining a plane perpendicular to the central, longitudinal axis of the bone screw), wherein the deployed circumferential recess is closer to the tip than the stowed circumferential recess.

In some embodiments, a bone screw assembly may comprise an annular bone screw race in the central cavity having a stowed position and a deployed position, the annular bone screw race comprising a first end, an outer circumferential surface comprising at least one circumferential nub (e.g., defining a plane perpendicular to the central, longitudinal axis of the bone screw) and at least one cam surface, and a second end opposite the first end, wherein the nub engages the stowed circumferential recess in the stowed position of the race and the nub engages the deployed circumferential recess in the deployed position of the race. A deployable protrusion may comprise a bone screw pin having a generally cylindrical shape and comprising a proximal end in mechanical communication with the at least one cam surface of the annular bone screw race and a distal end engage able with the at least one bone plate hole circumferential recess. An annular bone screw race, in some embodiments, may comprise a slot spanning its radial and longitudinal thickness). According to some embodiments, an annular bone screw race may comprise a central aperture comprising a central aperture surface, the central aperture surface comprising threads. An cam, in some embodiments, may comprise a first end having at least one cam notch. A cam slot may be distinct from or contiguous with at least one cam notch in some embodiments.

The present disclosure relates, in some embodiments, to methods for bone (e.g., vertebral) fixation. For example, a method may comprise contacting at least a portion of a spine (e.g., cervical spine) of a subject with a lockable bone plate assembly. A method, according to some embodiments, may comprise contacting at least one bone screw assembly of a lockable bone plate assembly with a bone of a subject, turning the at least one bone screw assembly (e.g., applying a torque to a torque surface) until it is secured in the bone (e.g., with threads at least partially embedded in the bone). In some embodiments, a method may comprise moving a deployable protrusion (e.g., from a stowed position) into a deployed position. A fixation method using a lockable back plate assembly having four bone screw assemblies may comprise, according to some embodiments, (a) contacting a first bone site with the first bone screw assembly; (b) turning the first bone screw assembly until it is secured in the first bone site; (c) moving a deployable protrusion in the first bone screw assembly into a deployed position, and/or (d) repeating (a), (b), and/or (c) for a second bone screw assembly and a second bone screw site, a third bone screw assembly and a third bone screw site, and/or a fourth bone screw assembly and a fourth bone screw site. Moving a deployable protrusion into a deployed position may comprise, in some embodiments, turning (e.g., applying a torque to a torque surface) a bone screw cap engaged with a bone screw cam such that the bone screw cam cams a deployable protrusion into a deployed position. Moving a deployable protrusion into a deployed position may comprise, in some embodiments, pressing a bone screw cam comprising a circumferential camming surface downwardly (e.g., toward the tip of the bone screw assembly) such that the circumferential camming surface cams a deployable protrusion (e.g., radially outwardly from a central, longitudinal axis of a bone screw) into a deployed position. In some embodiments, a method may comprise moving a deployable protrusion into a deployed position in which it engages at least a portion of a bone screw plate (e.g., a slot, recess, ridge, groove, indentation, and/or the like). For example, a method may comprise engaging a deployable protrusion in at least a portion of a bone screw plate in a way that limits, reduces, and/or prevents vertical movement (e.g., backout) of a bone screw assembly. A method may comprise, according to some embodiments, locking a deployable protrusion into a deployed position.

The present disclosure relates, in some embodiments, to a method of removing a lockable bone plate assembly comprising a bone screw assembly engaged in a bone, wherein the bone screw assembly comprises a deployable protrusion in a deployed position, the method comprising moving the deployable protrusion from the deployed position to a stowed position. For example, a method may comprise moving a deployable protrusion into a stowed position. According to some embodiments, moving a deployable protrusion into a stowed position may comprise turning (e.g., applying a torque to a torque surface) a bone screw cap engaged with a bone screw cam such that the bone screw cam disengages from the deployable protrusion, thereby freeing it to slide to a stowed position, for example, under the influence of radially, inwardly directed tension. Moving a deployable protrusion into a stowed position may comprise, in some embodiments, pulling a bone screw cam comprising a circumferential camming surface upwardly (e.g., away from the tip of the bone screw assembly) such that the bone screw cam disengages from the deployable protrusion, thereby freeing it to slide to a stowed position, for example, under the influence of radially, inwardly directed tension. Tension may arise, in some embodiments, from backout pressure exerted by the arrangement of a lockable back brace assembly relative to a bone, from turning the bone screw assembly to back it out of a bone plate and/or bone such that the distal tip of the deployable protrusion contacts (e.g., cams against) an inner surface of a bone plate through hole, and/or through compression forces exerted by a deployable protrusion notch sized to contact (e.g., squeeze) the deployable protrusion while in a deployed position.

BRIEF DESCRIPTION OF THE DRAWINGS

Some embodiments of the disclosure may be understood by referring, in part, to the present disclosure and the accompanying drawings, wherein:

FIG. 2A illustrates an exploded view of a bone screw assembly according to a specific example embodiment of the disclosure;

FIG. 6A illustrates a perspective view of a bone screw assembly in an undeployed position according to a specific example embodiment of the disclosure;

FIG. 6B illustrates a perspective view of a bone screw assembly in a deployed position according to a specific example embodiment of the disclosure;

FIG. 8B illustrates a perspective view of a bone screw according to a specific example embodiment of the disclosure;

FIG. 8C illustrates a perspective view of a bone screw cam according to a specific example embodiment of the disclosure;

FIG. 8D illustrates a perspective view of a bone screw cap according to a specific example embodiment of the disclosure;

FIG. 9A illustrates a perspective view of a bone screw assembly in an undeployed position according to a specific example embodiment of the disclosure;

FIG. 9B illustrates a perspective view of a bone screw assembly in a deployed position according to a specific example embodiment of the disclosure;

FIG. 9C illustrates a plan view of a bone screw assembly in an undeployed position according to a specific example embodiment of the disclosure;

FIG. 9D illustrates a plan view of a bone screw assembly in a deployed position according to a specific example embodiment of the disclosure;

FIG. 9E illustrates a section view of a bone screw assembly in an undeployed position according to a specific example embodiment of the disclosure;

FIG. 9F illustrates a section view of a bone screw assembly in a deployed position according to a specific example embodiment of the disclosure;

FIG. 12A illustrates a perspective view of a bone screw assembly in an undeployed position according to a specific example embodiment of the disclosure;

FIG. 12B illustrates a perspective view of a bone screw assembly in a deployed position according to a specific example embodiment of the disclosure;

FIG. 12C illustrates a plan view of a bone screw assembly in an undeployed position according to a specific example embodiment of the disclosure;

FIG. 12D illustrates a plan view of a bone screw assembly in a deployed position according to a specific example embodiment of the disclosure;

FIG. 12E illustrates a section view of a bone screw assembly in an undeployed position according to a specific example embodiment of the disclosure;

FIG. 12F illustrates a section view of a bone screw assembly in a deployed position according to a specific example embodiment of the disclosure;

Figure 1:
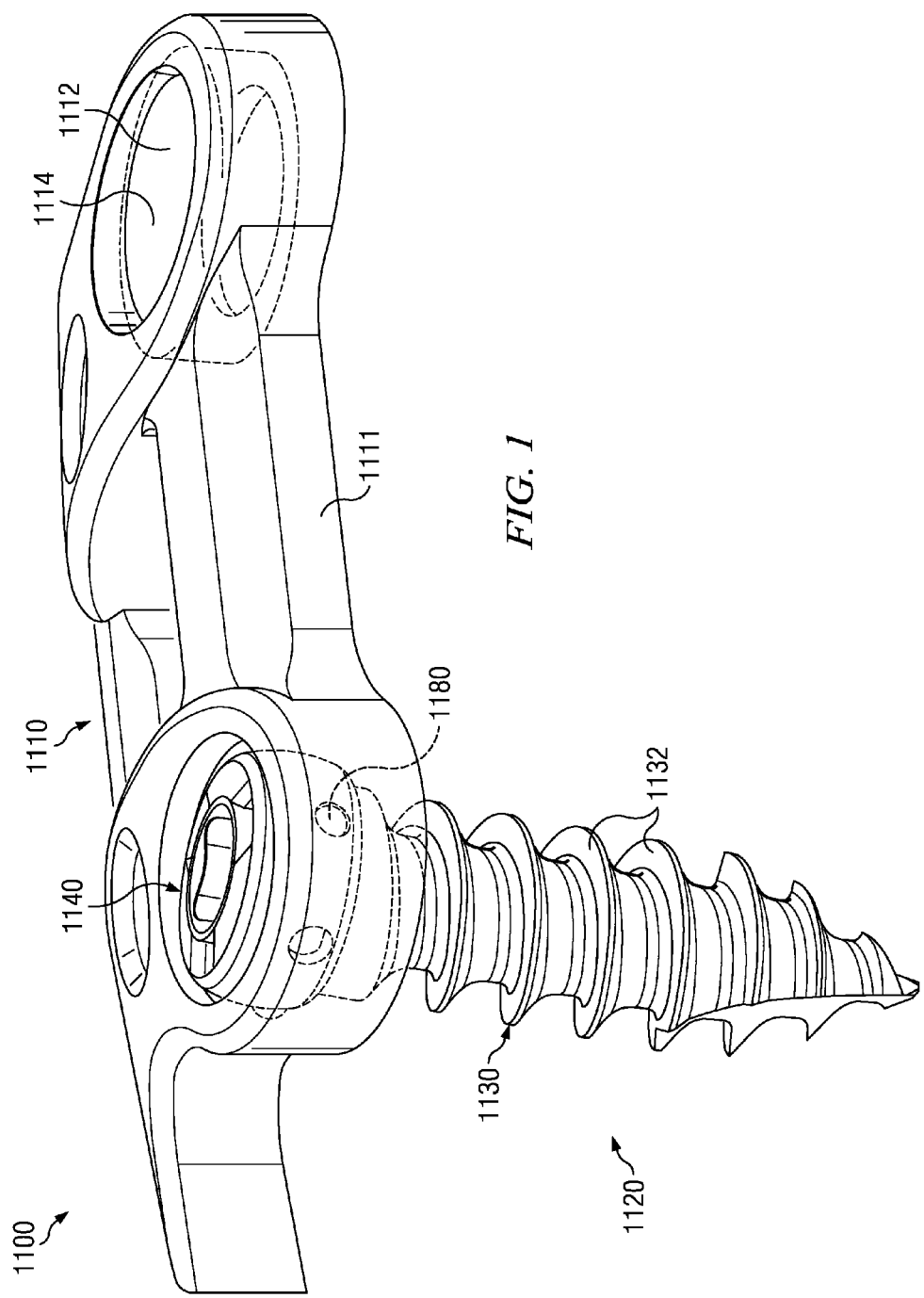
FIG. 1 illustrates a perspective view of a bone plate assembly according to a specific example embodiment of the disclosure.
Figure 2B:
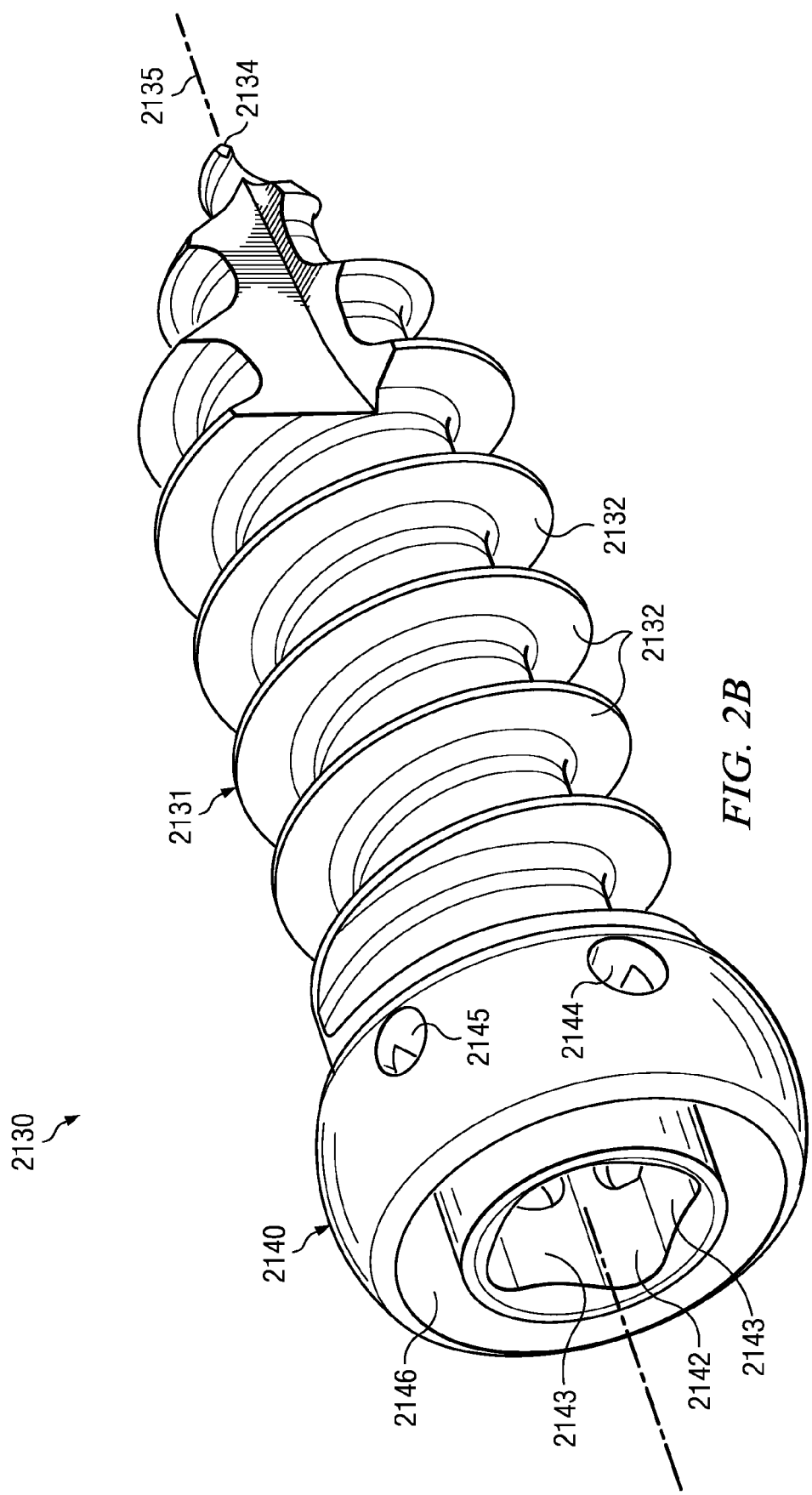
FIG. 2B illustrates a perspective view of a bone screw according to a specific example embodiment of the disclosure.
Figure 2C:
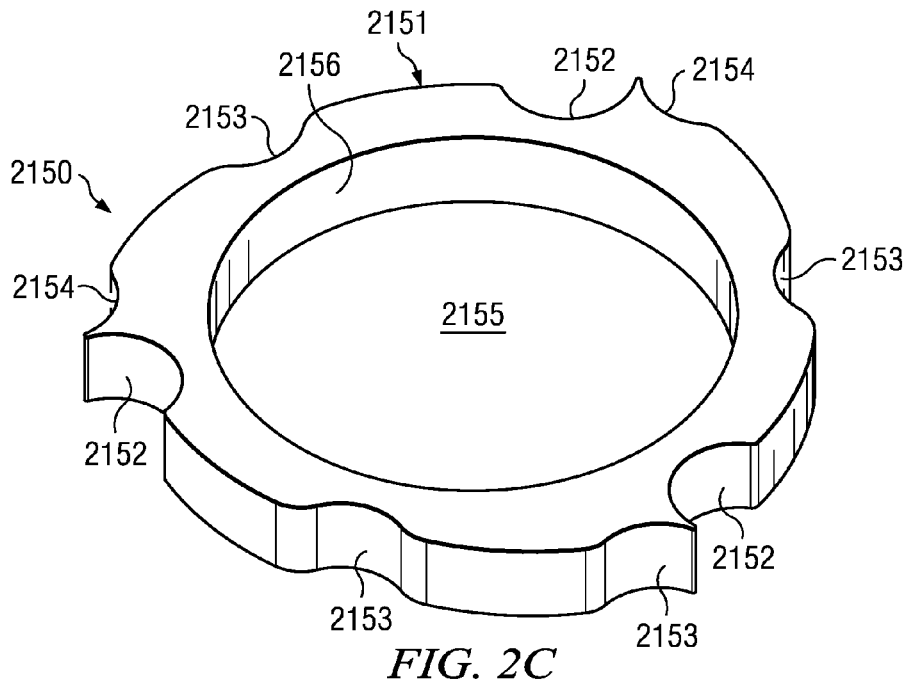
FIG. 2C illustrates a perspective view of a bone screw cam according to a specific example embodiment of the disclosure.
Figure 2D:
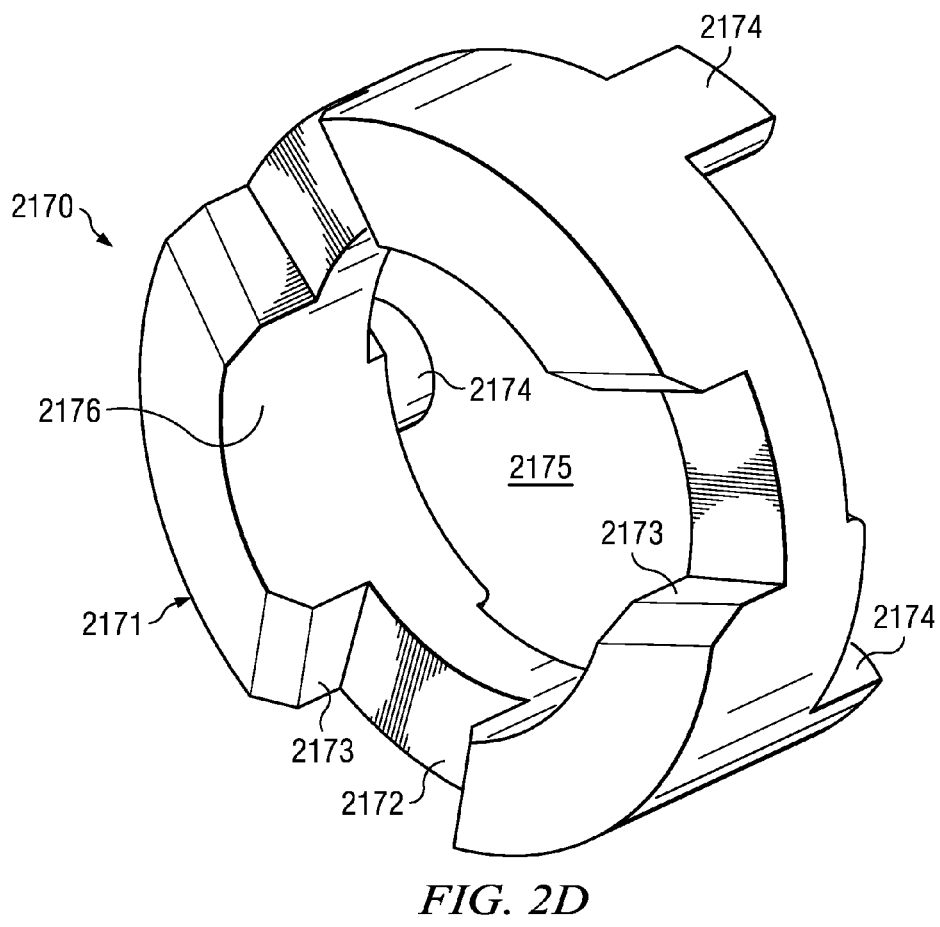
FIG. 2D illustrates a perspective view of a bone screw cap according to a specific example embodiment of the disclosure.

Table 1 below includes the reference numerals used in this disclosure in connection with specific example embodiments.

TABLE 1

| Reference Numerals | | | | |
|---|---|---|---|---|
| Bone Plate Assembly | 100 | 200 | 300 | 400 |
| Bone Plate | 110 | 210 | 310 | 410 |
| Body | 111 | 211 | 311 | 411 |
| Through Hole | 112 | 212 | 312 | 412 |
| Through Hole Recess | 113 | 213 | 313 | 413 |
| Through Hole Inner Surface | 114 | 214 | 314 | 414 |
| Through Hole Ridge | 115 | 215 | 315 | 415 |
| Mount | 116 | 216 | 316 | 416 |
| Aperture | 117 | 217 | 317 | 417 |
| Bone Screw Assembly | 120 | 220 | 320 | 420 |
| Bone Screw | 130 | 230 | 330 | 430 |
| Bone Screw Body | 131 | 231 | 331 | 431 |
| Threads | 132 | 232 | 332 | 432 |
| Threaded Portion | 133 | 233 | 333 | 433 |
| Bone Screw Tip | 134 | 234 | 334 | 434 |
| Central Axis | 135 | 235 | 335 | 435 |
| Bone Screw Head | 140 | 240 | 340 | 440 |
| Body | 141 | 241 | 341 | 441 |
| Notch | 142 | 242 | 342 | 442 |
| Torque Surface | 143 | 243 | 343 | 443 |
| Recess | 144 | 244 | 344 | 444 |
| Hole | 145 | 245 | 345 | 445 |
| Annular Groove | 146 | 246 | 346 | 446 |
| Stowed Circumferential Recess | 147 | 247 | 347 | 447 |
| Deployed Circumferential Recess | 148 | 248 | 348 | 448 |
| Stop | 149 | 249 | 349 | 449 |
| Bone Screw Cam | 150 | | | |
| Body | 151 | | | |
| Groove | 152 | | | |
| Deep Recess | 153 | | | |
| Shallow Recess | 154 | | | |
| Central Aperture | 155 | | | |
| Central Aperture Inner Surface | 156 | | | |
| Bone Screw Race | | 260 | 360 | 460 |
| Body | | 261 | 361 | 461 |
| Notch | | 262 | 362 | 462 |
| Notch Surface | | 263 | 363 | 463 |

TABLE 1-continued

Reference Numerals

| | | | |
|---|---|---|---|
| Cam Surface | 264 | 364 | 464 |
| Central Aperture | 265 | 365 | 465 |
| Central Aperture Inner Surface | 266 | 366 | 466 |
| Slot | 267 | 367 | 467 |
| Nub | 268 | 368 | 468 |
| Threads | | | 369 |
| Bone Screw Cap | 170 | | |
| Body | 171 | | |
| Notch | 172 | | |
| Torque Surface | 173 | | |
| Prong | 174 | | |
| Central Aperture | 175 | | |
| Central Aperture Inner Surface | 176 | | |
| Bone Screw Ball Bearing | 180 | | |
| Bone Screw Pin | 285 | 385 | 485 |
| Proximal End | 286 | 386 | 486 |
| Ridge | 287 | 387 | 487 |
| Distal End | 288 | 388 | 488 |

DETAILED DESCRIPTION

The present disclosure relates, in some embodiments, to locking mechanisms for a fastener (e.g., a bone screw) and associated devices, systems, and methods. For example, a device with a screw locking mechanism may comprise a bone plate assembly. A bone plate assembly may be easy to use in some embodiments. A bone plate assembly, according to some embodiments, may include a reversible locking mechanism. In some embodiments, a bone screw assembly may include a locking mechanism that does not rely solely on friction. A bone plate assembly may be secured, according to some embodiments, to a cervical plate (e.g., an anterior cervical plate).

Bone Plate Assembly

A bone plate assembly may permit at least partial load sharing between bones or bone sections that it connects. For example, a bone plate may permit at least partial sharing weight of vertebral bodies across a bone graft site. It may be desirable, in some embodiments, to permit some movement and/or weight to be borne by bone (e.g., to facilitate healing). According to some embodiments, a bone plate assembly may be strong enough to resist collapsing forces and/or abnormal angulation during the healing of a bone. It may be desirable, in some embodiments, for a bone plate assembly to be secure in its attachment to the spine (e.g., to resist and/or prevent migration of the implant or back out of the screws from the bone which could result in damage to the structures surrounding the spine, causing severe and potentially life threatening complications).

A bone plate assembly may comprise a bone screw assembly and a bone plate according to some embodiments. Optionally, a bone plate assembly may comprise, in some embodiments, a screw retaining member configured to cover at least a portion of one or more bone screws. For example, a screw retaining member may be provided with an aperture that receives a fastener (e.g., a screw) that fixes the screw retaining member to a bone plate. According to some embodiments, a bone plate assembly may be fastened to one or more bones. For example, a bone plate assembly may be fastened to a single bone (e.g., across a fracture or break) or to two or more bones (e.g., vertebrae). A bone plate may comprise one or more apertures (e.g., from 1 to about 10 apertures). Each aperture may receive a bone screw, which may be fitted into a drill hole, for example, to fasten the bone plate to bone.

Each member of a bone plate assembly independently may comprise one or more materials suitable for implantation in a subject (e.g., a human and/or a non-human animal). Each member of a bone plate assembly independently may comprise one or more materials capable of providing suitable structural and/or mechanical strength and/or integrity. Examples of suitable materials may include, without limitation, titanium, cobalt chromium, stainless steel, alloys thereof, and/or combinations thereof. Examples of suitable materials may include, without limitation, plastics, fibers (e.g., carbon fiber) and/or bioabsorbable materials. Each member of a bone plate assembly independently may comprise one or more one or more surface coatings (e.g., for drug delivery, to promote healing, to aid installation, to resist infection, to increase and/or reduce friction between components, and the like).

Bone Screw Assembly

A bone screw assembly may comprise, in some embodiments, a bone screw having a central, longitudinal axis, a deployable protrusion having a stowed position (e.g., substantially recessed within the bone screw) and a deployed position (e.g., at least a portion protrudes from the bone screw), and a protrusion driver in mechanical communication with the deployable protrusion. According to some embodiments, a protrusion driver may be in direct and/or indirect contact with a deployable protrusion. In some embodiments, a protrusion driver may be configured to displace a deployable protrusion from a stowed position to a deployed position. For example, a protrusion driver may displace a deployable protrusion radially outwardly, away from the central, longitudinal axis of a bone screw.

Bone Screw

According to some embodiments a bone screw may have a central longitudinal axis and comprise a bone screw body and a bone screw head. A bone screw body may be configured to be secured to a matrix (e.g., bone). For example, a bone screw body may comprise threads along at least a portion of its length.

A head may or may not have the same geometry and/or radius as a threaded portion. For example, it may have a shape other than round and/or may have a larger or smaller radius as compared to, for example, the average radius of a threaded portion, the minimum radius (e.g., sampled at or near the midpoint of a bone screw body longitudinal axis), the maximum radius, or any other radial metric of the threaded portion. A head may comprise, in some embodiments, one or more surfaces configured to receive a corresponding tool to fit (e.g., drive) a screw into position (e.g., screwed into and secured to a matrix). These one or more surfaces may be positioned anywhere on a head including, for example, near the center of a head and/or on a head's circumference.

According to some embodiments, a bone screw head may comprise at least one recess sized to house a deployable protrusion. For example, a recess may comprise a through hole (a) positioned approximately perpendicular to the center, longitudinal axis of a bone screw and/or (b) spaced away from the center, longitudinal axis of a bone screw. In some embodiments, a deployable protrusion may be positioned such that a portion of the protrusion is more proximal to the center, longitudinal axis of a bone screw and a portion of the protrusion is more distal to the center, longitudinal axis of a bone screw. For example, a stowed deployable protrusion may partially or completely occupy a through hole such that little or none of its distal portion protrudes from a bone screw head. In some embodiments, a proximal end of a deployable protrusion may be in mechanical communication (e.g., direct and/or indirect) with a protrusion driver. A protrusion driver may displace a deployable protrusion to a deployed position, for example, by exerting a force (e.g., a force directed radially outwardly) on the deployable protrusion's proximal end.

Deployable Protrusion

A deployable protrusion may have any desired size and/or shape. For example, it may be configured, in some embodiments, in any regular or irregular geometric shape including, without limitation, a sphere, a cylinder, a box, a torus, a cone, a prism, a disk, and/or combinations thereof. For example, a deployable protrusion may comprise a generally pin shape and/or a generally ball bearing shape. The size of a deployable protrusion may be scaled in proportion to the other parts with which it fits and/or in proportion to the bones to which a device containing the protrusion is to be affixed. A deployable protrusion may comprise any desired material. For example, a deployable protrusion may comprise a rigid or semi-rigid material capable of withstanding application of a shear force between a bone screw and a bone plate. A deployable protrusion may have one or more features including ridges, recesses, surface coatings, and/or combinations thereof according to some embodiments. For example, a deployable protrusion may have a feature (e.g., a circumferential ridge) configured to engage (e.g., contact) a stop in a bone screw head to hold it in a stowed position and/or a deployed position. A deployable protrusion may have a feature (e.g., a circumferential ridge) configured to engage (e.g., contact) a stop in a bone screw head to resist or prevent the protrusion form receding too far into a bone screw head or extending too far out of a bone screw head.

Protrusion Driver

According to some embodiments, a protrusion driver may have any desired size and/or shape. For example, it may be configured, in some embodiments, in any regular or irregular geometric shape including, without limitation, a sphere, a cylinder, a box, a torus, a cone, a prism, a disk, and/or combinations thereof. For example, a protrusion driver may comprise a generally torus shape. The size of a protrusion driver may be scaled in proportion to the other parts with which it fits and/or in proportion to the bones to which a device containing the protrusion is to be affixed. A protrusion driver may comprise any desired material. For example, a protrusion driver may comprise a rigid or semi-rigid material capable of supporting application of a force to a deployable protrusion (e.g., a force sufficient to displace the deployable protrusion into a deployed position and/or hold the deployable protrusion in a deployed position).

A protrusion driver may be configured, according to some embodiments, as a bone screw race. For example, a bone screw race may be configured to move (e.g., reversibly or irreversibly) parallel to the central, longitudinal axis of a bone screw and, in so doing, displace a deployable protrusion into a deployed position. In some embodiments, a protrusion driver may be configured as a bone screw cam. For example, a bone screw cam may be configured to rotate (e.g., reversibly or irreversibly) about the central, longitudinal axis of a bone screw and, in so doing, displace a deployable protrusion into a deployed position.

Bone Plate

According to some embodiments, a bone plate may be any object configured to receive two or more bone screw assemblies. A bone plate may comprise, in some embodiments, a rigid and/or semi-rigid body with at least two through holes, each configured to receive a bone screw assembly. A through hole may have a generally cylindrical shape and/or comprise one or more recesses and/or one or more protrusions. Each recess may be configured to engage a ball bearing, pin, or other protrusion from a bone screw assembly (e.g., from a bone screw assembly head). For example, each recess present may be positioned along the circumference (e.g., in a regular or irregular pattern if there is more than one recess) of a through hole.

Methods of Use

A bone screw assembly may be installed in a matrix (e.g., bone), in some embodiments, by drilling a hole in a bone, tapping the hole, and threading the bone screw assembly into the bone. According to some embodiments, drilling a hole may comprise holding a guide next to and/or attaching a guide to a bone and/or bone plate. For example, a drill may be inserted into a guide, a hole drilled into a bone, and the drill and guide removed. Care may be taken to ensure that a tap and/or a bone screw are inserted at substantially the same angle as the drill hole.

A method of installing a bone screw assembly comprising a bone screw, a deployable protrusion, and a protrusion driver may comprise, in some embodiments, inserting the bone screw assembly into a bone (e.g., in a pre-drilled hole in a bone) and manipulating the protrusion driver to deploy the deployable protrusion from a stowed position to a deployed position.

Methods of Therapy

The present disclosure relates, according to some embodiments, to a method of bone fixation (e.g., spinal fixation) may comprise. For example, a method may comprise installing a bone plate assembly having a locking mechanism (e.g., an anti-backout mechanism for component bone screws) in a subject. A method may comprise, in some embodiments, drilling a hole, tapping the hole, and threading a bone screw into a bone. A method may comprise installing a self-drilling screw without pre-drilling and/or without tapping according to some embodiments. A guide may be held next to or attached to a plate in some embodiments. A drill may be inserted, according to some embodiments, into the guide and the hole drilled into the bone. A guide, if used, may be removed and a tap may be threaded through the hole (e.g., following the same or substantially the same angle as a drill hole. It may be desirable to proceed with caution, for example, to prevent the sharp edges of the tap from damaging surrounding tissues or in creating too large a tap hole by toggling the handle of the tap. This damage may reduce the security of the screw bite into the bone and/or increase the likelihood of screw pullout. After tapping, a screw may be guided at a proper angle into a hole that has been created. In some embodiments, inadvertent misalignment may reduce pullout strength and/or may result in damage to surrounding nerves or arteries.

In some embodiments, a method may comprise contacting a bone plate assembly comprising at least one fastener with a bone of subject, inserting the fastener in the bone, locking the fastener, and combinations thereof. For example, inserting and locking, optionally may be repeated for up to all of the fasteners in the bone plate assembly. Locking a fastener comprising at least one protrusion and at least one protrusion driver in mechanical communication with the at least one protrusion may comprise moving (e.g., rotating and/or sliding) the protrusion driver such that is moves the at least one or more protrusions into at least partial engagement with a bone plate (e.g., a bone plate detent, bone plate groove, bone plate recess, bone plate slot, bone plate well, bone plate hole, bone plate channel, and/or the like).

A method of bone fixation may be used to address (e.g., prevent, treat, ameliorate, ease, and/or relieve) one or more conditions and/or symptoms thereof. Conditions that may be addressed include, according to some embodiments, traumatic conditions, pathological conditions, developmental conditions, degenerative conditions, and/or combinations thereof. For example, a method of bone fixation may be used to address degenerative disc disease, spondylolisthesis, a bone fracture or break, spinal stenosis, deformities (e.g., scoliosis, kyphosis and/or lordosis), tumor, pseudoartrosis, necrosis, a bulging or herniated disc, and combinations thereof. In some embodiments, a method of bone fixation may be applied to any bone(s) in a subject body. A method may be applied, for example, to a subject's cervical spine (e.g., C2-C7). A healthcare professional exercising reasonable prudence and care may determine which embodiment is most desirable for a particular subject.

Specific Example Embodiments

FIG. 1 illustrates a perspective view of bone plate assembly 1100 according to a specific example embodiment of the disclosure. As shown bone plate assembly 1100 comprises bone plate 1110 and bone screw assembly 1120. Bone plate 1110 comprises body 1111, through holes 1112, mount 1116, and aperture 1117. Each through hole 1112 defines a central, longitudinal axis generally perpendicular to the plane of body 1111 (e.g., and/or ±~5° and/or ±~20°). Each through hole 1112 comprises inner surface 1114 having recess 1113 and ridge 1115. Recess 1113 may extend along the entire circumference of inner surface 1114 and/or lie in a plane generally perpendicular to the central, longitudinal axis of through hole 1112. Bone screw assembly 1120 comprises bone screw 1130, threads 1132, cam 1150, cap 1170, and ball bearings 1180. Bone screw assembly 1120 is fitted into one of through holes 1112 with each ball bearing 1180 in a deployed position, engaged in through hole recess 1113. According to some embodiments, one or more of recesses 1113 may be sized the same as or just slightly larger than the size of ball bearing 1180. Bone plate assembly 1100 may comprise, in some embodiments, a like number of bone screw assemblies 1120 and through holes 1112.

A bone screw assembly 2120 may comprise bone screw 2130, deployable protrusion 2180, protrusion driver 2150, and, optionally, cap 2170, according to some embodiments (e.g., FIGS. 2A-2D). Bone screw 2130 may comprise body 2131 and bone screw head 2140. Bone screw body 2131 may have one or more threads 2132 spanning threaded portion 2133, which may be configured to advance and/or fix bone screw 2130 in a hole in a matrix (e.g., bone). For example, threads 2132 may spirally surround the outer longitudinal circumference of body 2131, tapering to tip 2134. Bone screw body 2130 may have central, longitudinal axis 2135.

Bone screw head 2140 may comprise notch 2142, torque surface 2143, through holes 2144, through holes 2145, and annular groove 2146. Notch 2142 may be configured to rotate about an axis parallel to and/or rotate in a plane generally perpendicular to longitudinal axis 2135 of bone screw 2130. Notch 2142 may be configured to receive a mated installation tool (e.g., a screwdriver, a torx, an Allen key (e.g., 4-, 5-, or 6-sided)). Upon application of a force (e.g., torque) to torque surface 2143, bone screw 2130 may rotate about its central longitudinal axis 2135 and, optionally, propel tip 2134 into a matrix (e.g., bone). Annular groove 2146 may surround notch 2142. Annular groove 2146 may lie in a plane generally perpendicular to longitudinal axis 2135 of bone screw 2130 and/or generally parallel to the rotational plane of notch 2142. Holes 2144 may receive ball bearings 2180. Each hole 2144 and/or each hole 2145 may independently have a longitudinal axis that is perpendicular to center, longitudinal axis 2135 of bone screw 2130. Each hole 2144 may independently have a diameter that is uniform along its full length. In some embodiments, each hole 2144 may independently have a narrowing at or near the end more distal to center, longitudinal axis 2135 of bone screw 2130. Holes 2144 and 2145 may be distributed at regular intervals, as shown, or irregular intervals around the circumference of bone screw head 2140. Bone screw 2130 may be a single piece or two or more conjoined parts according to some embodiments.

Bone screw cam 2150 may fit (e.g., rotatably fit) within annular groove 2146. For example, cam 2150 may fit within annular groove 2146 such that it may rotate about and/or rotate in a plane generally perpendicular to longitudinal axis 2135 of bone screw 2130. Cam 2150 may rotate clockwise and/or counterclockwise in some embodiments. Cam 2150 may be generally circular (e.g., annular) with a diameter greater (e.g., much greater) than it's thickness. Cam 2150 may comprise body 2151, which may itself define and/or comprise central aperture 2155. Central aperture 2155 may surround notch 2142. Cam 2150 may comprise grooves 2152, deep recesses 2153, and/or shallow recesses 2154, for example, along its outer edge. Each recess 2153 and/or each recess 2154 may independently contact one or more ball bearings 2180.

Bone screw cap 2170 may fit (e.g., rotatably fit) within annular groove 2146. For example, cap 2170 may fit within annular groove 2146 such that it may rotate about and/or rotate in a plane generally perpendicular to longitudinal axis 2135 of bone screw 2130. Cap 2170 may rotate clockwise and/or counterclockwise in some embodiments. Cap 2170 may be generally circular (e.g., annular) with a diameter greater (e.g., much greater) than it's thickness. Cap 2170 may comprise body 2171, which may itself define and/or comprise central aperture 2175. Central aperture 2175 may surround notch 2142. Cap 2170 may comprise notch 2172, torque surface 2173, and prong 2174. Each notch 2172 may span the radial thickness of body 2171. Two or more notches 2172 may be positioned on the same face of cap 2170 as one another. Two or more prongs 2174 may be positioned on the same face of cap 2170 as one another. One or more notches 2172 may be positioned on the opposite face of cap 2170 as one or more prongs 2174. Each prong 2174 may independently contact (e.g., fit within) a groove 2152 on bone screw 2130. Cap may engage cam 2150 (e.g., through contact between grooves 2152 and prongs 2174) such that a force (e.g., torque) applied to notch 2174 (e.g., via torque surface 2173) may rotate not only cap 2170, but also cam 2150. Cap 2170 may comprise one or more features (e.g., welds, swags, and/or others) that secure it to bone screw 2130, for example, to retain itself, cam 2150, and/or bearings 2180 in desirable and/or functional relation to bone screw 2130.

Figure 3A:
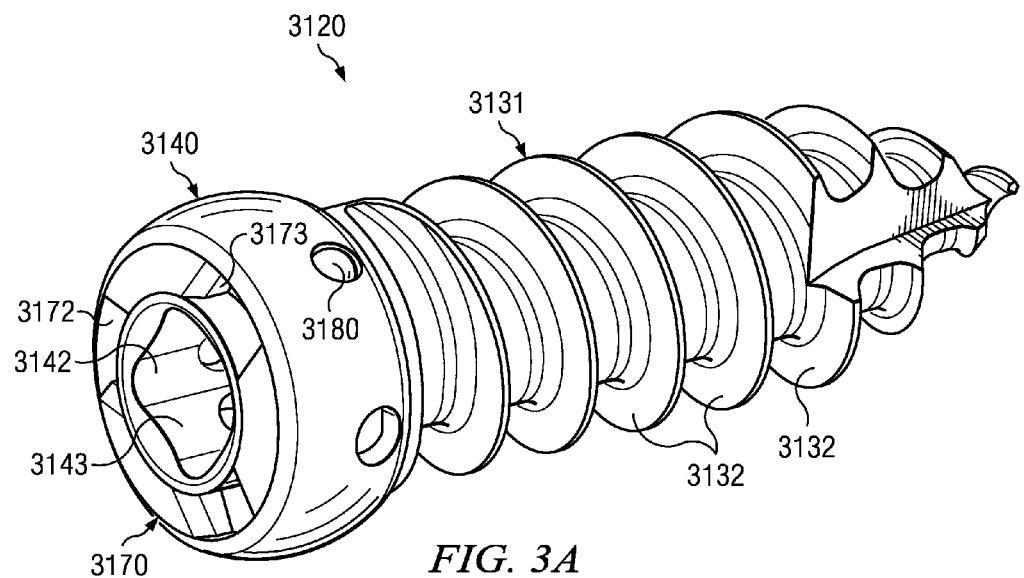
FIG. 3A illustrates a perspective view of a bone screw assembly in an undeployed position according to a specific example embodiment of the disclosure.
Figure 3B:
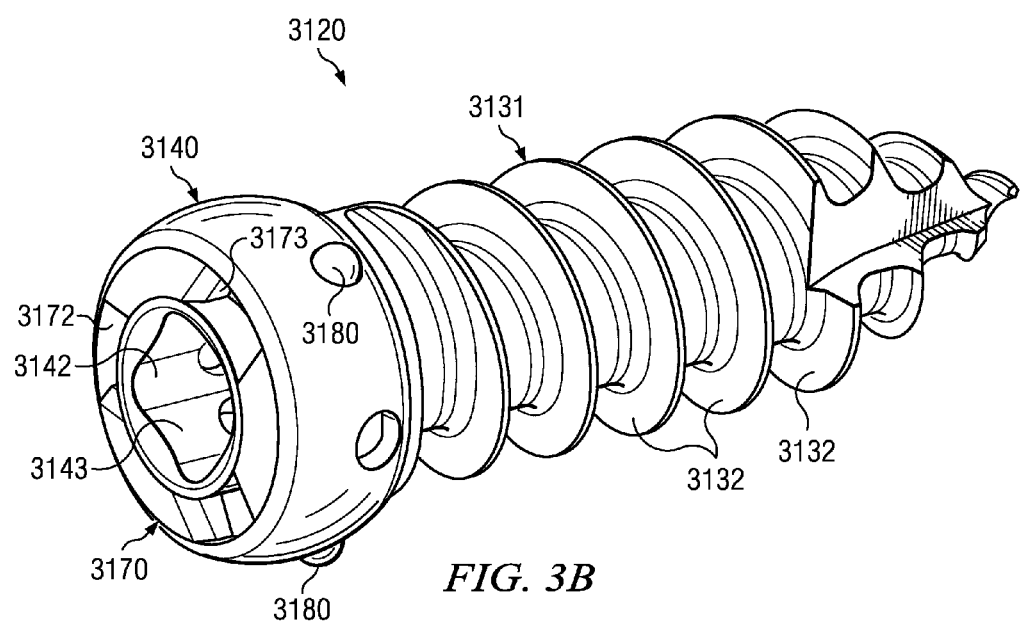
FIG. 3B illustrates a perspective view of a bone screw assembly in a deployed position according to a specific example embodiment of the disclosure.
Figure 3C:
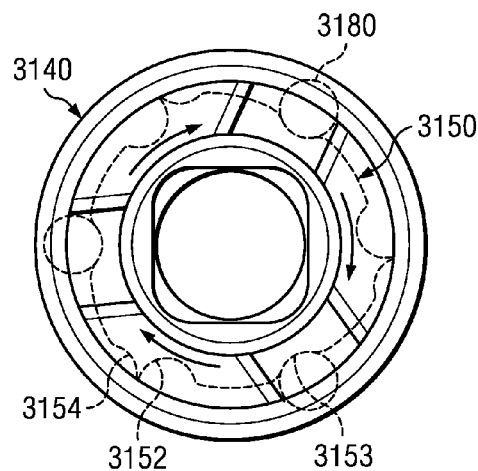
FIG. 3C illustrates a plan view of a bone screw assembly in an undeployed position according to a specific example embodiment of the disclosure.
Figure 3D:
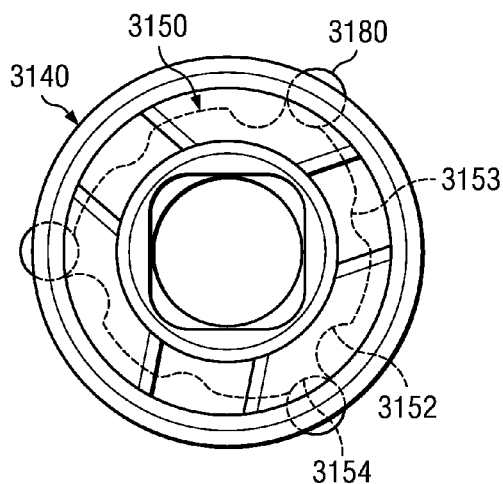
FIG. 3D illustrates a plan view of a bone screw assembly in a deployed position according to a specific example embodiment of the disclosure.
Figure 3E:
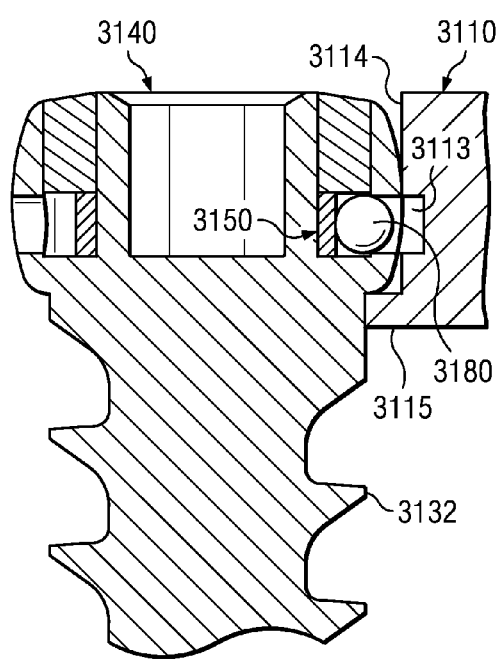
FIG. 3E illustrates a section view of a bone screw assembly in an undeployed position according to a specific example embodiment of the disclosure.
Figure 3F:
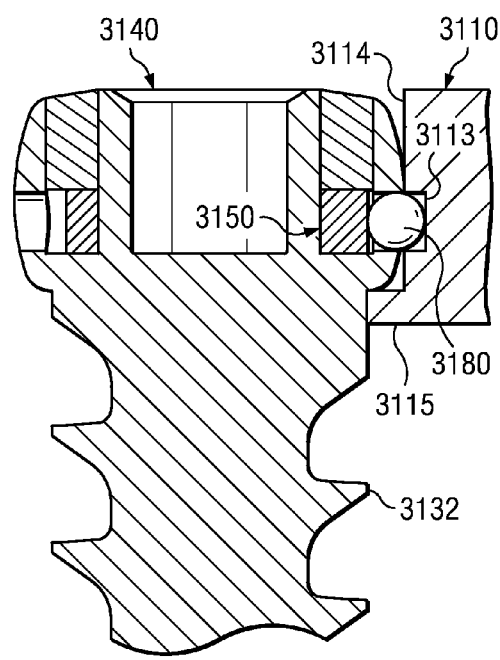
FIG. 3F illustrates a section view of a bone screw assembly in a deployed position according to a specific example embodiment of the disclosure.

FIGS. 3A-3F illustrate perspective, plan, and section views of bone screw assembly 3120 with ball bearings in a stowed position (FIGS. 3A, 3C, and 3E) and a deployed position (FIGS. 3B, 3D, and 3F). As shown, each ball bearing 3180 in an undeployed position may (a) occupy a hole 3144, (b) engage a deep recess 2153 such that its outer edge is substantially flush with the outer surface of head 3140, and/or (c) have little or no opportunity for contact with plate 2110 (FIGS. 3A, 3C, and 3E). Each ball bearing 3180 in a deployed position may (a) partially occupy a hole 3144, (b) engage a shallow recess 3154 such that it protrudes from hole 3144 beyond the outer surface of head 3140, and/or (c) has sufficient exposure to contact plate 3110 (FIGS. 3B, 3D, and 3F).

In use, each ball bearing 3180 may be deployed upon rotation (e.g., clockwise or counterclockwise) of cam 3150 from a position that permits engagement of each ball bearing 3180 with a deep recess 3153 to a position that permits engagement of each ball bearing 3180 with a shallow recess 3154. Rotation of cam 3150 may be achieved by application of a force (e.g., a torque) to notch 3172 (e.g., via torque surface 3173), which drives rotation of prongs 3174 and, in turn, rotation of engaged grooves 3152. FIG. 3C illustrates a plan view of a bone screw assembly in an undeployed position according to a specific example embodiment of the disclosure. As shown, ball bearings 3180 are engaged with deep recesses 3153. A tool (not pictured) may be inserted into notches 3172 and rotated clockwise (arrows), displacing bearings 3180 radially outwardly. This rotation may continue until ball bearings 3180 engage shallow recesses 3154; at which point bearings 3180 come to rest in a deployed position (FIG. 3D). If present, recess 3153 may permit screw assembly 3120 to "lock" into an undeployed position (e.g., due to recess 3153's contour and/or the resiliency of the material of which screw assembly 3120 is constructed). If present, recess 3154 may permit screw assembly 3120 to "lock" into a deployed position (e.g., due to recess 3154's contour and/or the resiliency of the material of which screw assembly 3120 is constructed). If desired, bone screw assembly 3120 may be removed by unlocking (e.g., counter-rotating) cam 3150 and backing out (e.g., counter-rotating) bone screw 3130.

Figure 4:
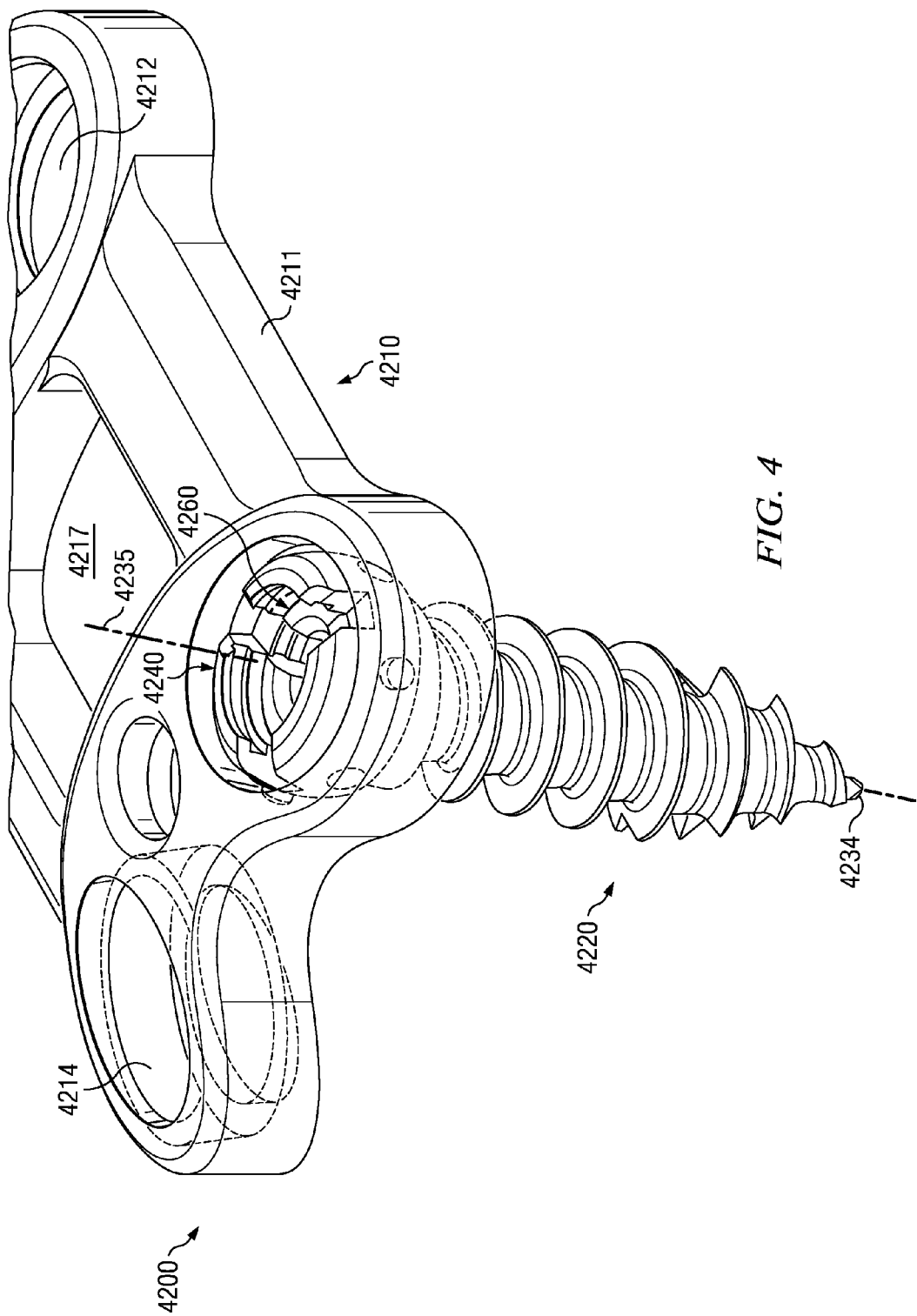
FIG. 4 illustrates a perspective view of a bone plate assembly according to a specific example embodiment of the disclosure.

FIG. 4 illustrates a perspective view of bone plate assembly 4200 according to a specific example embodiment of the disclosure. As shown bone plate assembly 4200 comprises bone plate 4210 and bone screw assembly 4220. Bone plate 4210 comprises body 4211, through holes 4212, mount 4216, and aperture 4217. Each through hole 4212 defines a central, longitudinal axis generally perpendicular to the plane of body 4211 (e.g., and/or ±~5° and/or ±~20°). Each through hole 4212 comprises inner surface 4214 having recess 4213 and ridge 4215. Recess 4213 may extend along the entire circumference of inner surface 4214 and/or lie in a plane generally perpendicular to central, longitudinal axis of through hole 4212. Bone screw assembly 4220 comprises bone screw 4230, threads 4232, race 4260, and bone screw pin 4285. Bone screw assembly 4220 is fitted into one of through holes 4212 with each bone screw pin 4285 in a deployed position, engaged in through hole recess 4213. According to some embodiments, one or more of recesses 4213 may be sized the same as or just slightly larger than the size of bone screw pins 4285. Bone plate assembly 4200 may comprise, in some embodiments, a like number of bone screw assemblies 4220 and through holes 4212.

A bone screw assembly 5220 may comprise bone screw 5230, deployable protrusion 5285, and protrusion driver 5260 according to some embodiments (e.g., FIGS. 5A-5D). Bone screw 5230 may comprise body 5231 and bone screw head 5240. Bone screw body 5231 may have one or more threads 5232 spanning threaded portion 5233, which may be configured to advance and/or fix bone screw 5230 in a hole in a matrix (e.g., bone). For example, threads 5232 may spirally surround the outer longitudinal circumference of body 5231, tapering to tip 5234. Bone screw body 5230 may have central, longitudinal axis 5235.

Figure 5A:
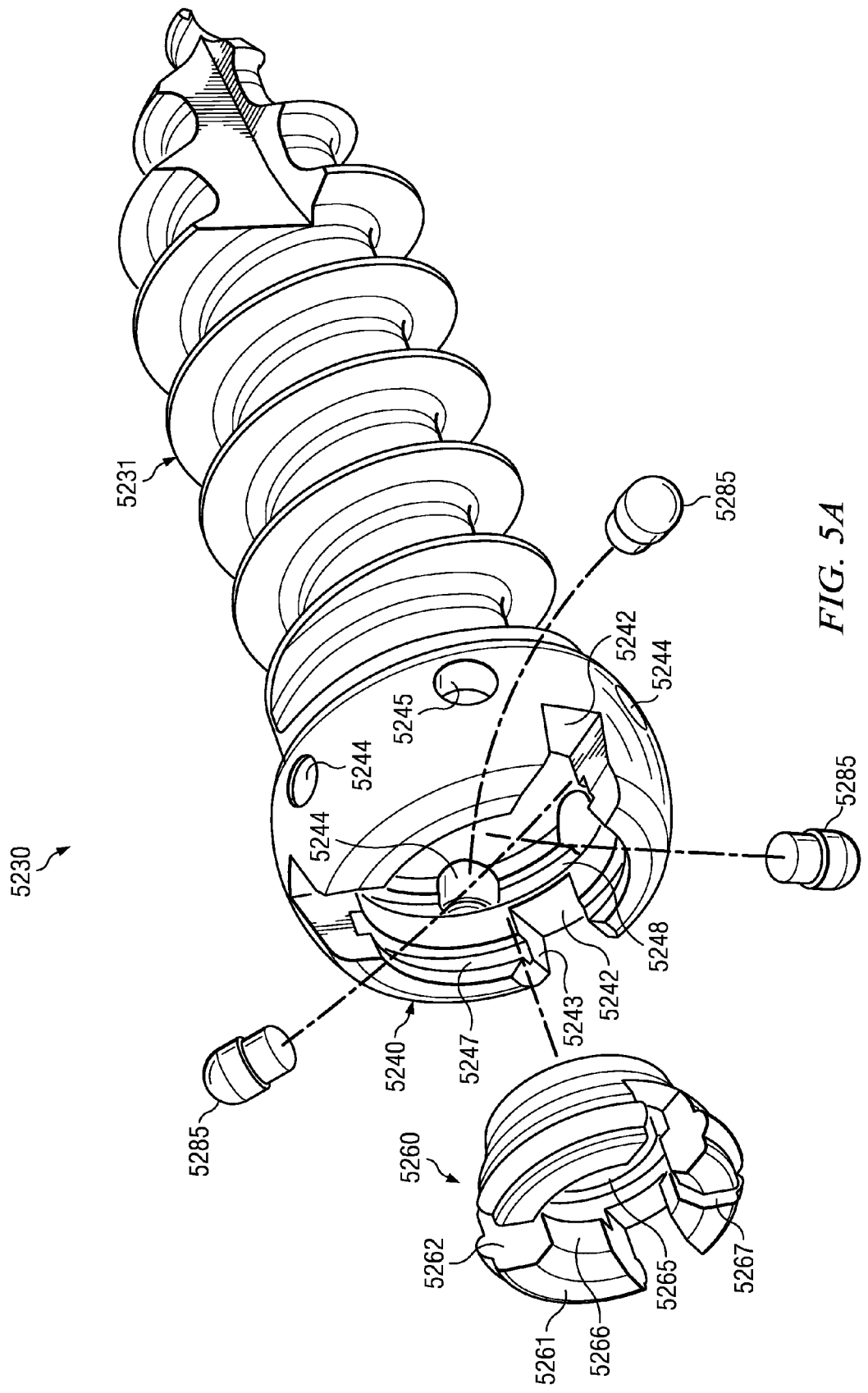
FIG. 5A illustrates an exploded view of a bone screw assembly according to a specific example embodiment of the disclosure.
Figure 5B:
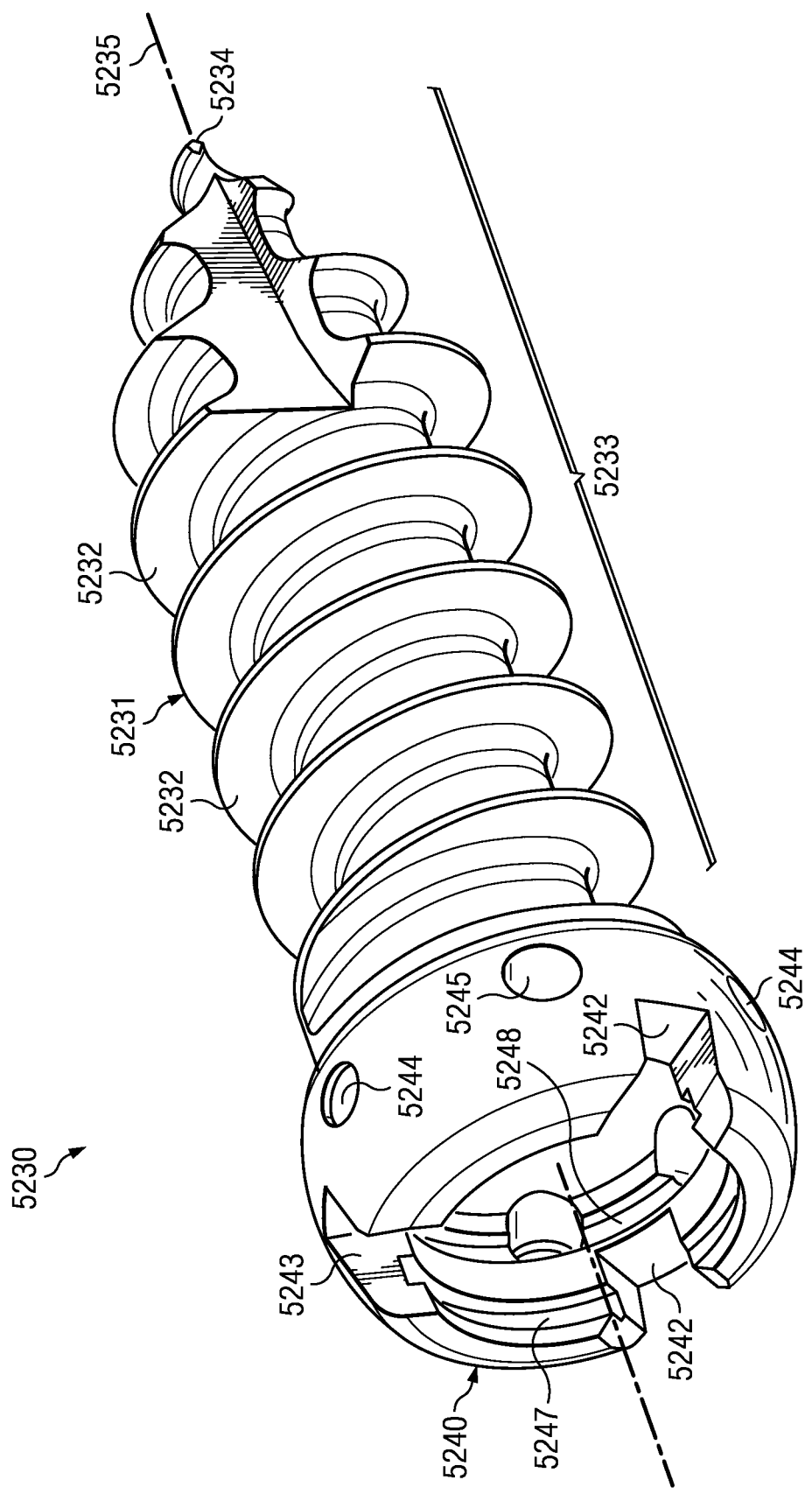
FIG. 5B illustrates a perspective view of a bone screw according to a specific example embodiment of the disclosure.
Figure 5C:
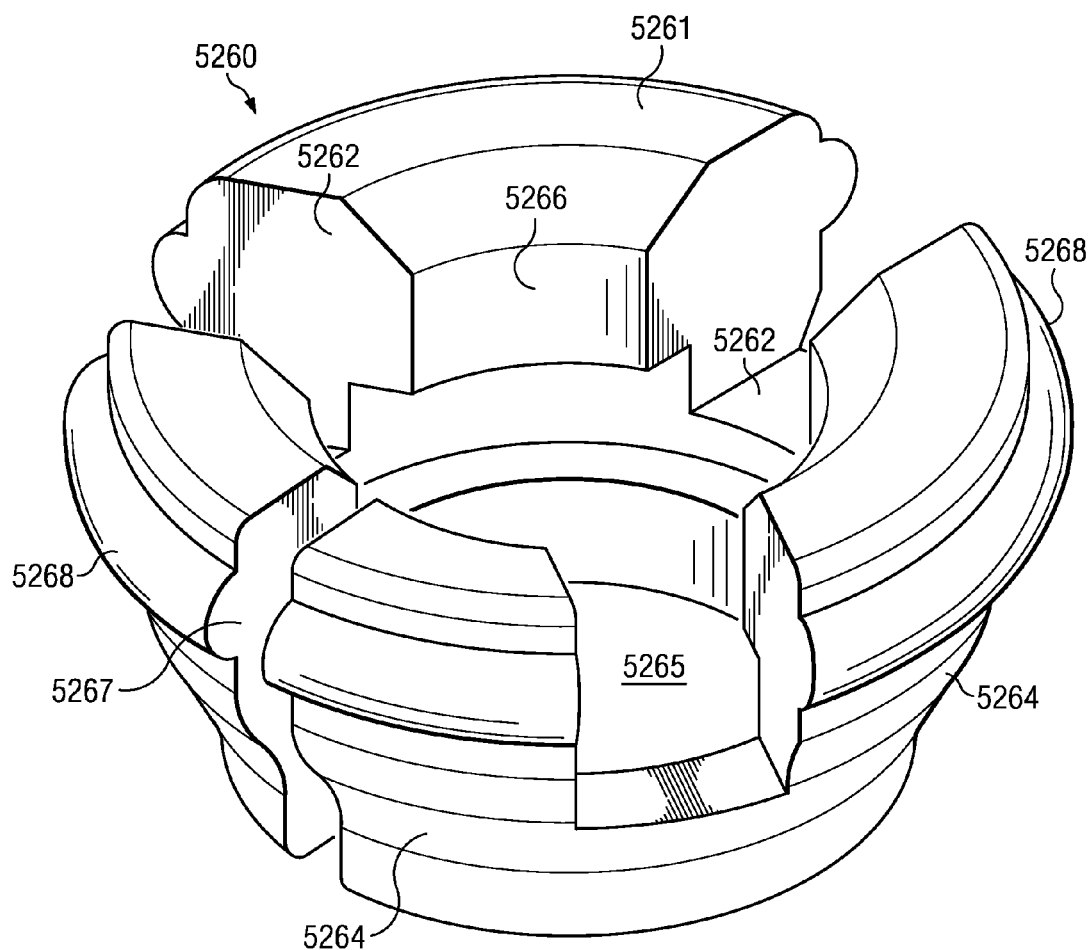
FIG. 5C illustrates a perspective view of a bone screw cam according to a specific example embodiment of the disclosure.
Figure 5D:
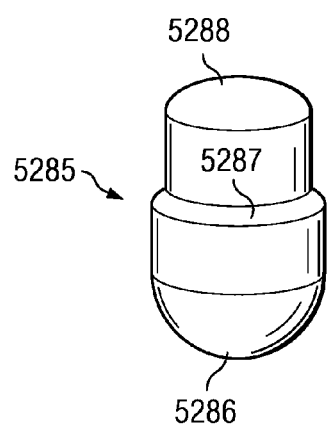
FIG. 5D illustrates a perspective view of a bone screw cap according to a specific example embodiment of the disclosure.

Bone screw head 5240 may comprise notch 5242, torque surface 5243, through holes 5244, through holes 5245, stowed circumferential recess 5247, and deployed circumferential recess 5248. Notch 5242 may be configured to rotate about an axis parallel to and/or rotate in a plane generally perpendicular to longitudinal axis 5235 of bone screw 5230. Each notch 5242 may span the radial thickness of body 5241. Notches 5242 may be configured to receive a mated installation tool (e.g., a cylinder with axially protruding circumferential pins dimensioned to engage notches 5242 and/or surfaces 5243). Upon application of a force (e.g., torque) to torque surface 5243, bone screw 5230 may rotate about central longitudinal axis 5235 and, optionally, propel tip 5234 into a matrix (e.g., bone). Stowed circumferential recess 5247, and deployed circumferential recess 5248 may lie in a plane generally perpendicular to longitudinal axis 5235 of bone screw 5230 and/or generally parallel to the rotational plane of notch 5242. Deployed circumferential recess 5248 may be positioned closer to tip 5234 and/or more distant from the apex of bone screw 5230 than stowed circumferential recess 5247. Holes 5244 may receive bone screw pins 5285 (e.g., from their interior faces as illustrated in FIG. 5A). Each hole 5244 and/or each hole 5245 may independently have a longitudinal axis that is perpendicular to center, longitudinal axis 5235 of bone screw 5230. Each hole 5244 may independently have a diameter that is uniform along its full length. In some embodiments, each hole 5244 may independently have a narrowing at or near the end more distal to center, longitudinal axis 5235 of bone screw 5230. Holes 5244 and 5245 may be distributed at regular intervals, as shown, or irregular intervals around the circumference of bone screw head 5240. Bone screw 5230 may be a single piece or two or more conjoined parts according to some embodiments.

Bone screw race 5260 may comprise body 5261, notches 5262, each with surfaces 5263, cam surface 5264, central aperture 5265, central aperture inner surface 5266, slot 5267, and/or nub 5268. Body 5261 may itself define and/or comprise central aperture 5265 and/or may taper at one end. In some embodiments, race 5260 may be solid and lack central aperture 5265. Race 5260 may be generally circular (e.g., annular) with a diameter greater than it's thickness. Each notch 5262 may span the radial thickness of body 5261 and/or only a portion of the longitudinal thickness of body 5261. Two or more notches 5262—may be positioned on the same face of race 5260 as one another and/or opposite of cam surface 5264. Slot 5267 may span both the radial and longitudinal thickness of body 5261 (e.g., defining a gap in an otherwise annular structure). Slot 5267 may permit (e.g., independently or in cooperation with the resiliency of race 5260 and/or bone screw head 5240) race 5260 to be radially compressed (e.g., temporarily). This may facilitate movement of race 5260 between stowed positions and deployed positions and/or installation of race 5260 in bone screw 5230. Slot 5267 may be separate from (as shown) or contiguous with a notch 5262. Race 5260 may fit (e.g., slidably fit) within a cavity in bone screw head 5240 (e.g., at or near the apex of bone screw 5230). For example, race 5260 may fit within bone screw head 5230 such that it may slide (e.g., reversibly) along longitudinal axis 5235 of bone screw 5230. Race 5260 may be positioned within bone screw head 5240 such that nub 5268 engages stowed circumferential recess 5247 (stowed position) or deployed circumferential recess 5248 (deployed position). As shown, race 5260 may be positioned such that it is flush with bone screw head 5240 (its surface farthest from tip 5234 is level with the surface of bone screw head 5240 that is farthest from tip 5234) in a stowed position. When moved to a deployed position, race 5260 is depressed into bone screw head 5240. Alternatively, race 5260 may be positioned such it is above bone screw head 5240 in a stowed position. When moved to a deployed position, race 5260 then becomes flush with bone screw head 5240. Cam surface 5264 may independently contact one or more bone screw pins 5285.

Bone screw pin 5285 may have a generally cylindrical shape and/or comprise proximal end 5286, ridge 5287, and distal end 5288. Proximal end 5286 may be flat or domed. Distal end 5288 may be flat or domed. Proximal end 5286 may be positioned more proximal to central axis 5235 than distal end 5288. Ridge 5267 may engage stop 5249 (e.g., when pin 5285 is in a deployed position.

Figure 6C:
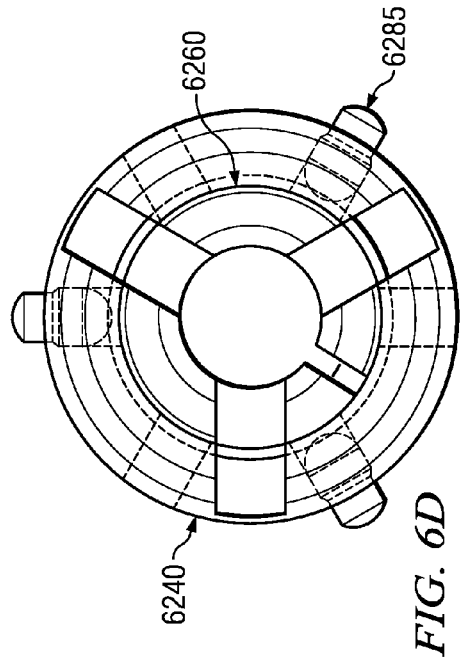
FIG. 6C illustrates a plan view of a bone screw assembly in an undeployed position according to a specific example embodiment of the disclosure.
Figure 6E:
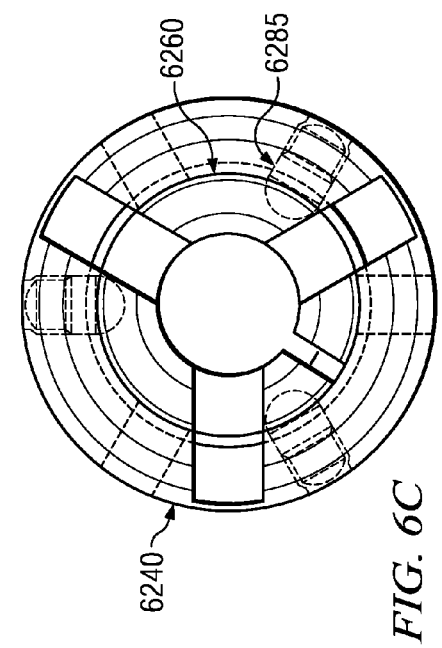
FIG. 6E illustrates a section view of a bone screw assembly in an undeployed position according to a specific example embodiment of the disclosure.
Figure 6D:
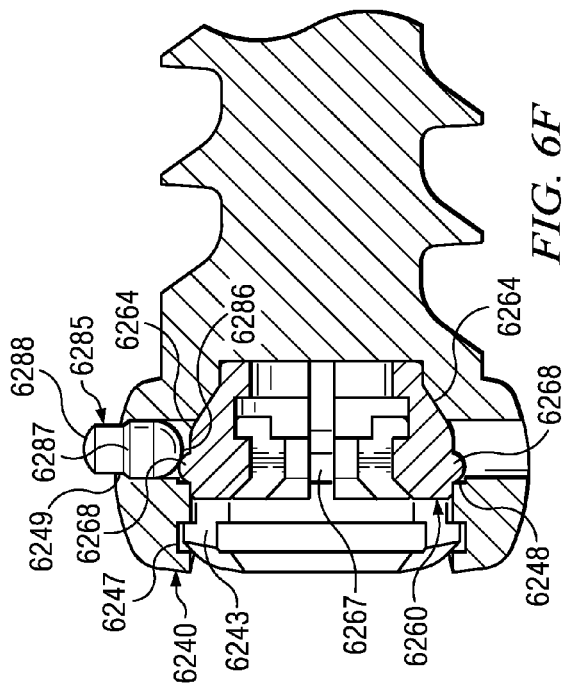
FIG. 6D illustrates a plan view of a bone screw assembly in a deployed position according to a specific example embodiment of the disclosure.
Figure 6F:
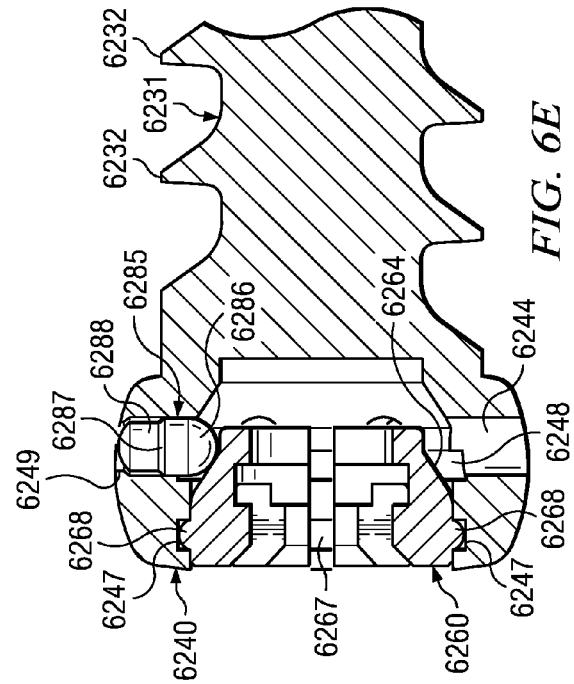
FIG. 6F illustrates a section view of a bone screw assembly in a deployed position according to a specific example embodiment of the disclosure.

FIGS. 6A-6F illustrate perspective, plan, and section views of bone screw assembly 6220 with bone screw pins 6285 in a stowed position (FIGS. 6A, 6C, and 6E) and a deployed position (FIGS. 6B, 6D, and 6F). As shown, each bone screw pin 6285 in an undeployed (or stowed) position may (a) occupy a hole 6244, (b) engage a deep recess 6253 such that its outer edge is substantially flush with the outer surface of head 6240, and/or (c) have little or no opportunity for contact with plate 6210 (FIGS. 6A, 6C, and 6E). Each bone screw pin 6285 in a deployed position may (a) partially occupy a hole 6244, (b) engage a shallow recess 6254 such that it protrudes from hole 6244 beyond the outer surface of head 6240, and/or (c) has sufficient exposure to contact plate 6210 (FIGS. 6B, 6D, and 6F).

In use, each bone screw pin 6285 may be deployed upon application of a force generally along and/or parallel to central axis 6235 and directed toward tip 6234. Race 6260 may slide (e.g., snap) from a stowed position more distant from tip 6234 to a deployed position closer to tip 6234 in which nub 6268 moves from engagement with stowed circumferential recess 6247 to engagement with deployed circumferential recess 6248. Such movement may slide cam surface 6264 across proximal end 6286 and displace (e.g., cam) bone screw pins 6285 radially outwardly from a stowed position to a deployed position. A tool (not pictured) may be inserted into notches 6262 and used to drive race 6260 towards tip 6235. This may continue until nub 6268 engages recess 6248; at which point pins 6285 come to rest in a deployed position (FIG. 6D). If present, recess 6247 may permit screw assembly 6220 to "lock" into an undeployed position (e.g., due to recess 6247's contour and/or the resiliency of the material of which screw assembly 6220 is constructed). If present, recess 6248 may permit screw assembly 6220 to "lock" into a deployed position (e.g., due to recess 6248's contour and/or the resiliency of the material of which screw assembly 6220 is constructed). If desired, bone screw assembly 6220 may be removed by unlocking race 6250 (e.g., by inserting a tool into the center of the race, engaging the tool with an undercut in the center bore of the race, and pulling the race up to the undeployed position) and backing out (e.g., counter-rotating) bone screw 6230.

Figure 7:
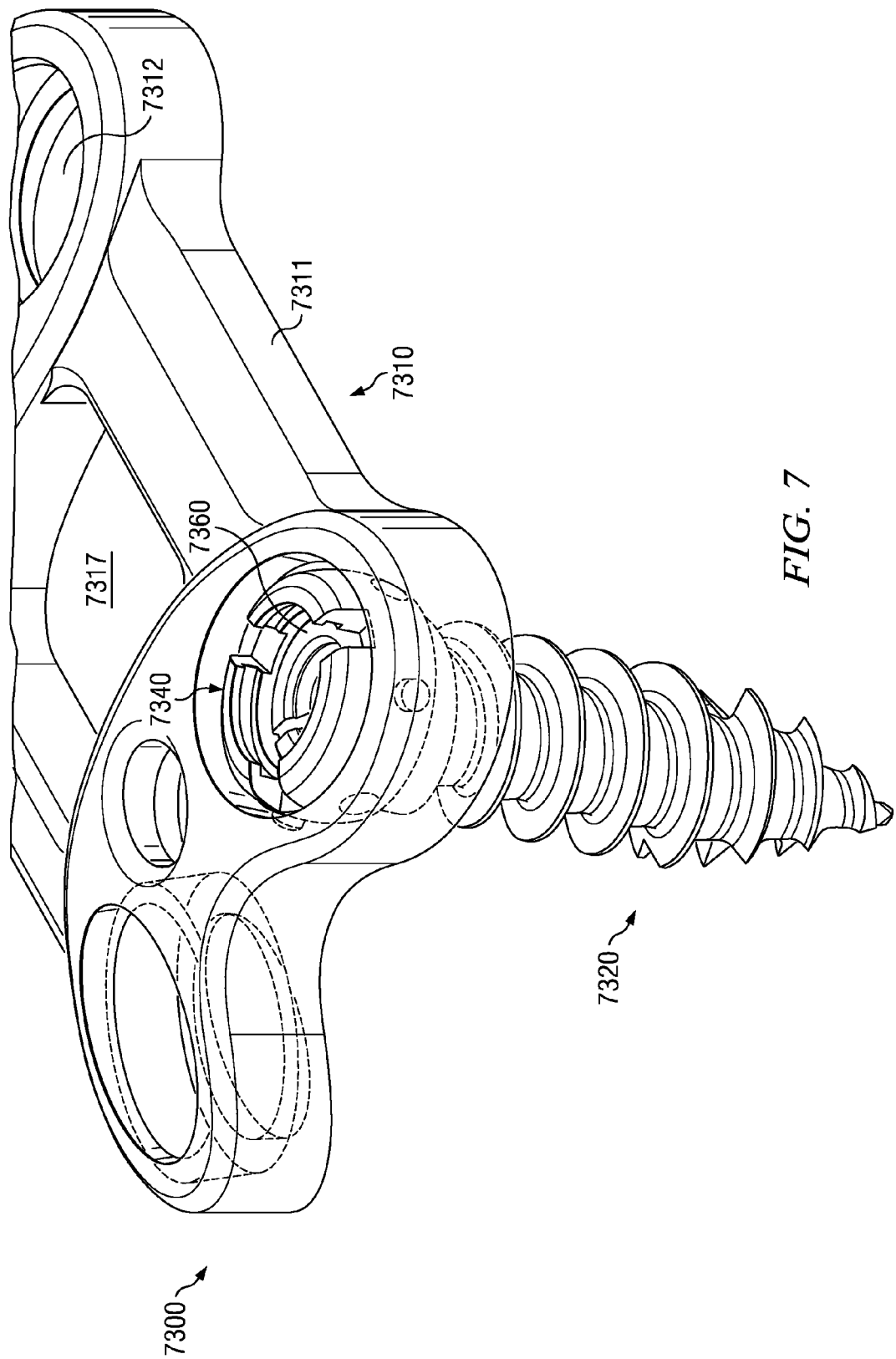
FIG. 7 illustrates a perspective view of a bone plate assembly according to a specific example embodiment of the disclosure.

FIG. 7 illustrates a perspective view of bone plate assembly 7300 according to a specific example embodiment of the disclosure. As shown bone plate assembly 7300 comprises bone plate 7310 and bone screw assembly 7320. Bone plate 7310 comprises body 7311, through holes 7312, mount 7316, and aperture 7317. Each through hole 7312 defines a central, longitudinal axis generally perpendicular to the plane of body 7311 (e.g., and/or ±~5° and/or ±~20°). Each through hole 7312 comprises inner surface 7314 having recess 7313 and ridge 7315. Recess 7313 may extend along the entire circumference of inner surface 7314 and/or lie in a plane generally perpendicular to central, longitudinal axis of through hole 7312. Bone screw assembly 7320 comprises bone screw 7330, threads 7332, race 7360, and bone screw pin 7385. Bone screw assembly 7320 is fitted into one of through holes 7312 with each bone screw pin 7385 in a deployed position, engaged in through hole recess 7313. According to some embodiments, one or more of recesses 7313 may be sized the same as or just slightly larger than the size of bone screw pins 7385. Bone plate assembly 7300 may comprise, in some embodiments, a like number of bone screw assemblies 7320 and through holes 7312.

A bone screw assembly 8320 may comprise bone screw 8330, deployable protrusion 8385, and protrusion driver 8360 according to some embodiments (e.g., FIGS. 8A-8D). Bone screw 8330 may comprise body 8331 and bone screw head 8340. Bone screw body 8331 may have one or more threads 8332 spanning threaded portion 8333, which may be configured to advance and/or fix bone screw 8330 in a hole in a matrix (e.g., bone). For example, threads 8332 may spirally surround the outer longitudinal circumference of body 8331, tapering to tip 8334. Bone screw body 8330 may have central, longitudinal axis 8335.

Figure 8A:
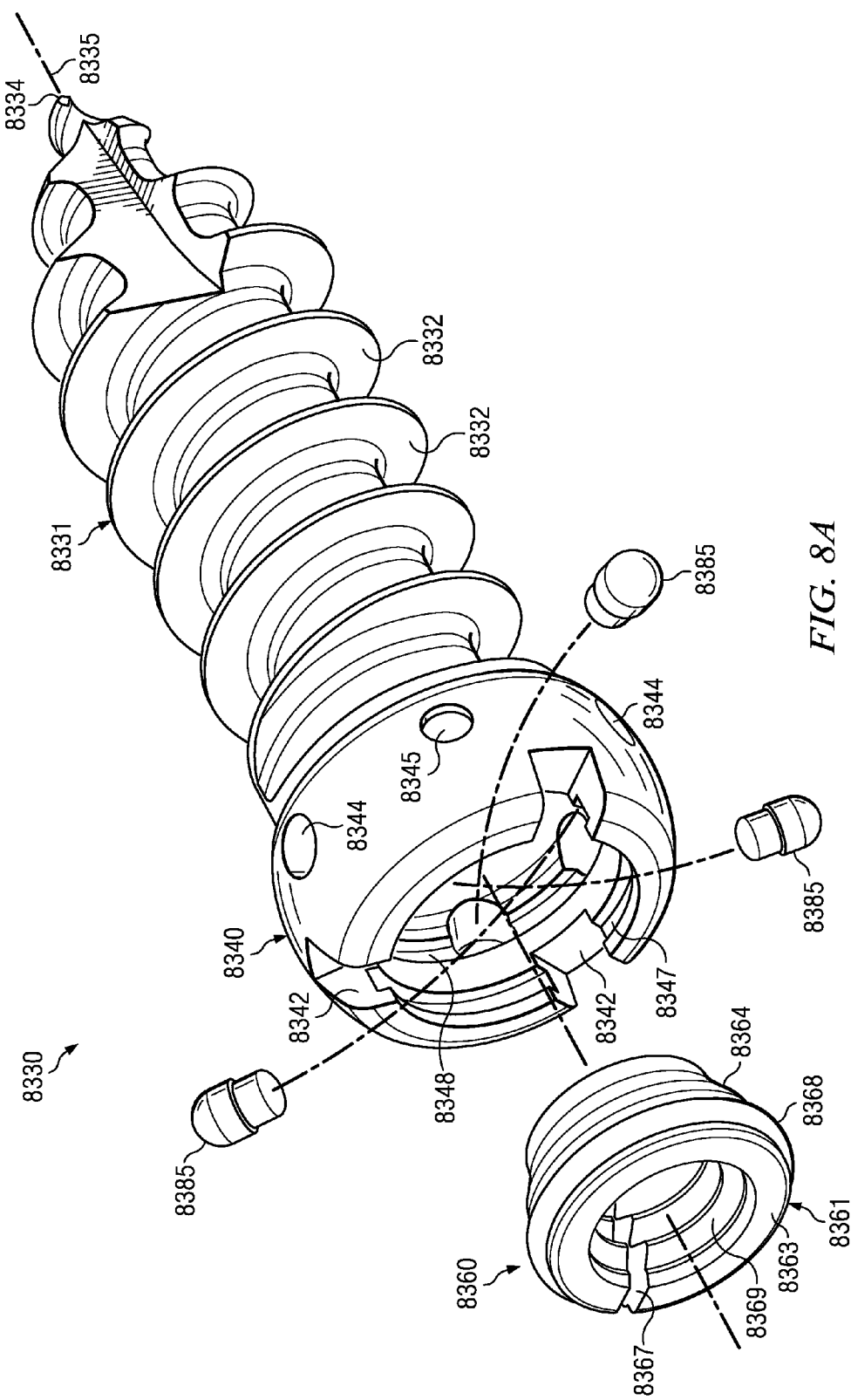
FIG. 8A illustrates an exploded view of a bone screw assembly according to a specific example embodiment of the disclosure.

Bone screw head 8340 may comprise notch 8342, torque surface 8343, through holes 8344, through holes 8345, stowed circumferential recess 8347, and deployed circumferential recess 8348. Notch 8342 may be configured to rotate about an axis parallel to and/or rotate in a plane generally perpendicular to longitudinal axis 8335 of bone screw 8330. Each notch 8342 may span the radial thickness of body 8341. Notches 8342 may be configured to receive a mated installation tool (e.g., a cylinder with axially protruding circumferential pins dimensioned to engage notches 8342 and/or surfaces 8343). Upon application of a force (e.g., torque) to torque surface 8343, bone screw 8330 may rotate about central longitudinal axis 8335 and, optionally, propel tip 8334 into a matrix (e.g., bone). Stowed circumferential recess 8347, and deployed circumferential recess 8348 may lie in a plane generally perpendicular to longitudinal axis 8335 of bone screw 8330 and/or generally parallel to the rotational plane of notch 8342. Deployed circumferential recess 8348 may be positioned closer to tip 8334 and/or more distant from the apex of bone screw 8330 than stowed circumferential recess 8347. Holes 8344 may receive bone screw pins 8385 (e.g., from their interior faces as illustrated in FIG. 8A). Each hole 8344 and/or each hole 8345 may independently have a longitudinal axis that is perpendicular to center, longitudinal axis 8335 of bone screw 8330. Each hole 8344 may independently have a diameter that is uniform along its full length. In some embodiments, each hole 8344 may independently have a narrowing at or near the end more distal to center, longitudinal axis 8335 of bone screw 8330. Holes 8344 and 8345 may be distributed at regular intervals, as shown, or irregular intervals around the circumference of bone screw head 8340. Bone screw 8330 may be a single piece or two or more conjoined parts according to some embodiments.

Bone screw race 8360 may comprise body 8361, surface 8363, cam surface 8364, central aperture 8365, central aperture inner surface 8366, slot 8367, nub 8368, and/or threads 8369 (along inner surface 8366). Body 8361 may itself define and/or comprise central aperture 8365 and/or may taper at one end. Race 8360 may be generally circular (e.g., annular) with a diameter greater than it's thickness. Slot 8367 may span both the radial and longitudinal thickness of body 8361 (e.g., defining a gap in an otherwise annular structure). Slot 8367 may permit (e.g., independently or in cooperation with the resiliency of race 8360 and/or bone screw head 8340) race 8360 to be radially compressed (e.g., temporarily). This may facilitate movement of race 5260 between stowed positions and deployed positions and/or installation of race 8360 in bone screw 8330.

Race 8360 may fit (e.g., slidably fit) within a cavity in bone screw head 8340 (e.g., at or near the apex of bone screw 8330). For example, race 8360 may fit within bone screw head 8330 such that it may slide (e.g., reversibly) along longitudinal axis 8335 of bone screw 8330. Race 8360 may be positioned within bone screw head 8340 such that nub 8368 engages stowed circumferential recess 8347 (stowed position) or deployed circumferential recess 8348 (deployed position). As shown, race 8360 may be positioned such that it is flush with bone screw head 8340 (its surface 8363 farthest from tip 8334 is level with the surface of bone screw head 8340 that is farthest from tip 8334) in a stowed position. When moved to a deployed position, race 8360 is depressed into bone screw head 8340. Alternatively, race 8360 may be positioned such it is above bone screw head 8340 in a stowed position. When moved to a deployed position, race 8360 then becomes flush with bone screw head 8340. Cam surface 8364 may independently contact one or more bone screw pins 8385.

Bone screw pin 8385 may have a generally cylindrical shape and/or comprise proximal end 8386, ridge 8387, and distal end 8388. Proximal end 8386 may be flat or domed. Distal end 8388 may be flat or domed. Proximal end 8386 may be positioned more proximal to central axis 8335 than distal end 8388. Ridge 8367 may engage stop 8349 (e.g., when pin 8385 is in a deployed position.

FIGS. 9A-9F illustrate perspective, plan, and section views of bone screw assembly 9320 with bone screw pins 9385 in a stowed position (FIGS. 9A, 9C, and 9E) and a deployed position (FIGS. 9B, 9D, and 9F). As shown, each bone screw pin 9385 in an undeployed (or stowed) position may (a) occupy a hole 9344, (b) engage a deep recess 9353 such that its outer edge is substantially flush with the outer surface of head 9340, and/or (c) have little or no opportunity for contact with plate 9310 (FIGS. 9A, 9C, and 9E). Each bone screw pin 9385 in a deployed position may (a) partially occupy a hole 9344, (b) engage a shallow recess 9354 such that it protrudes from hole 9344 beyond the outer surface of head 9340, and/or (c) has sufficient exposure to contact plate 9310 (FIGS. 9B, 9D, and 9F).

In use, each bone screw pin 9385 may be deployed upon application of a force generally along and/or parallel to central axis 9335 and directed toward tip 9334. Race 9360 may slide (e.g., snap) from a stowed position more distant from tip 9334 to a deployed position closer to tip 9334 in which nub 9368 moves from engagement with stowed circumferential recess 9347 to engagement with deployed circumferential recess 9348. Such movement may slide cam surface 9364 across proximal end 9386 and displace (e.g., cam) bone screw pins 9385 radially outwardly from a stowed position to a deployed position. A tool (not pictured) may be inserted into central aperture 8365 such that it engages threads 8369 and used to drive race 9360 towards tip 9335. A tool for engaging central aperture 8365 may comprise, for example, a threaded tip that resembles a screw. This may continue until nub 9368 engages recess 9348; at which point pins 9385 come to rest in a deployed position (FIG. 9D). If present, recess 9347 may permit screw assembly 9320 to "lock" into an undeployed position (e.g., due to recess 9347's contour and/or the resiliency of the material of which screw assembly 9320 is constructed). If present, recess 9348 may permit screw assembly 9320 to "lock" into a deployed position (e.g., due to recess 9348's contour and/or the resiliency of the material of which screw assembly 9320 is constructed). If desired, bone screw assembly 9320 may be removed by unlocking race 9360 (e.g., pulling it axially away from tip 9334) and backing out (e.g., counter-rotating) bone screw 9330.

Figure 10A:
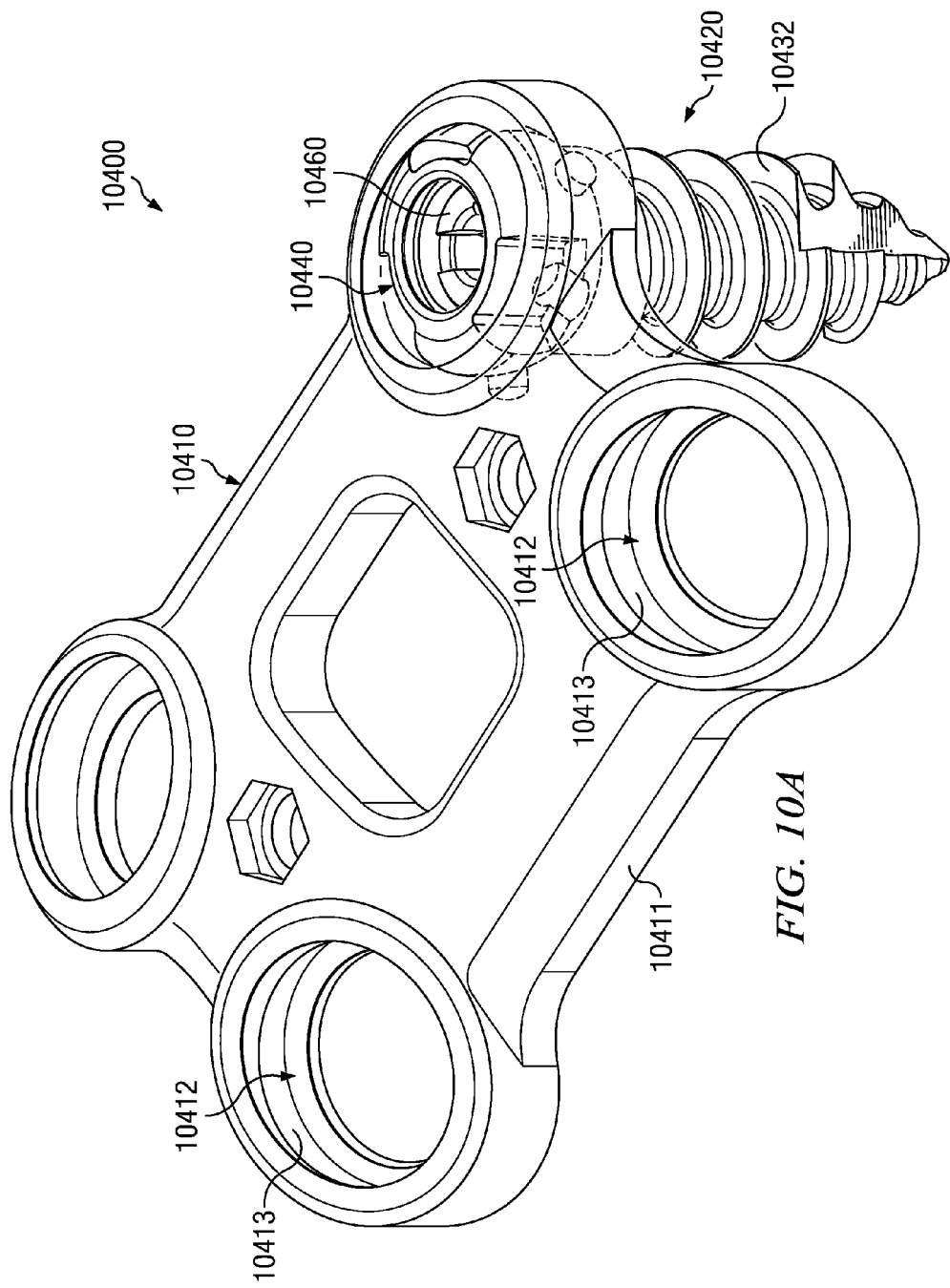
FIG. 10A illustrates a perspective view of a bone plate assembly according to a specific example embodiment of the disclosure.
Figure 10B:
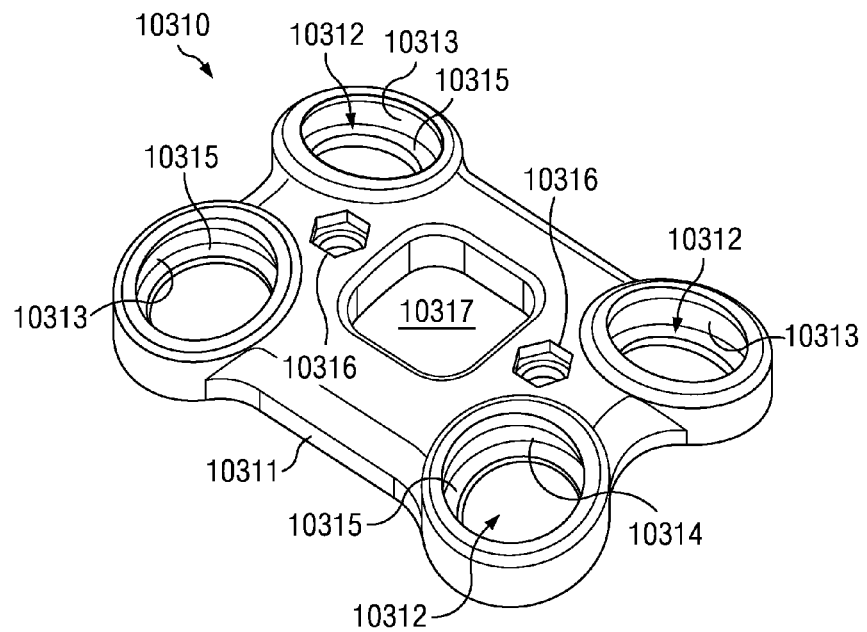
FIG. 10B illustrates a perspective view of a bone plate according to a specific example embodiment of the disclosure.
Figure 10C:
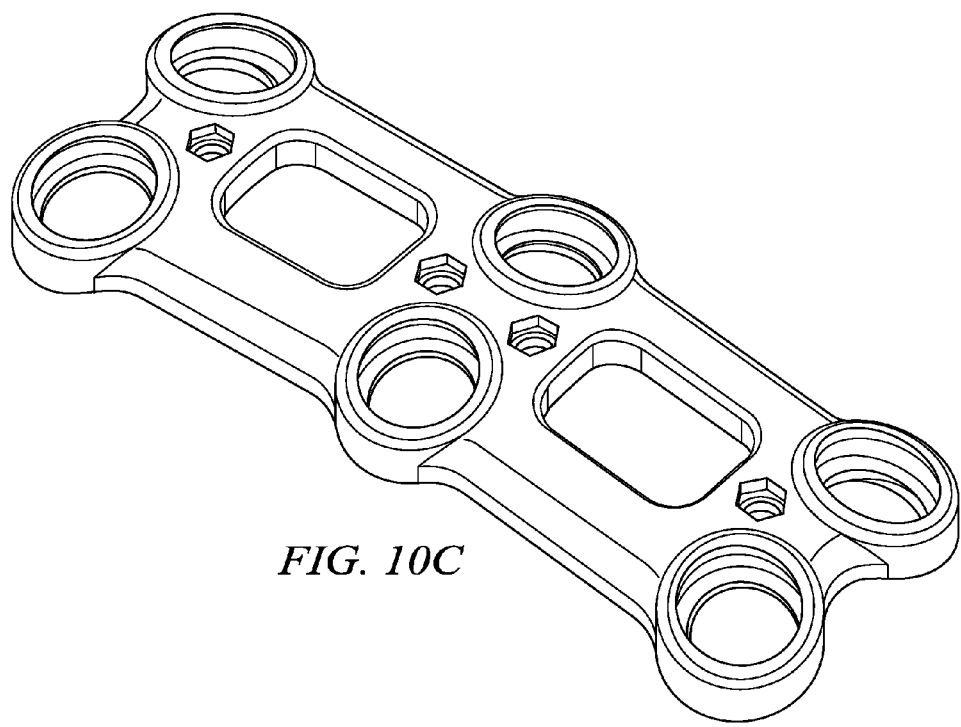
FIG. 10C illustrates a perspective view of a bone plate according to a specific example embodiment of the disclosure.

FIG. 10A illustrates a perspective view of bone plate assembly 10400 according to a specific example embodiment of the disclosure. As shown bone plate assembly 10400 comprises bone plate 10410 and bone screw assembly 10420. Bone plate 10410 comprises body 10411, through holes 10412, mount 10416, and aperture 10417 (FIG. 10B). Bone plate assembly 10400 may comprise 4 through holes 10412 (FIGS. 10A and 10B) or 6 through holes 10412 (FIG. 10C). Each through hole 10412 defines a central, longitudinal axis generally perpendicular to the plane of body 10411 (e.g., and/or ±~5° and/or ±~20°). Each through hole 10412 comprises inner surface 10414 having recess 10413 and ridge 10415. Recess 10413 may extend along the entire circumference of inner surface 10414 and/or lie in a plane generally perpendicular to central, longitudinal axis of through hole 10412. Bone screw assembly 10420 comprises bone screw 10430, threads 10432, race 10460, and bone screw pin 10485. Bone screw assembly 10420 is fitted into one of through holes 10412 with each bone screw pin 10485 in a deployed position, engaged in through hole recess 10413. According to some embodiments, one or more of recesses 10413 may be sized the same as or just slightly larger than the size of bone screw pins 10485. Bone plate assembly 10400 may comprise, in some embodiments, a like number of bone screw assemblies 10420 and through holes 10412.

A bone screw assembly 11420 may comprise bone screw 11430, deployable protrusion 11485, and protrusion driver 11460 according to some embodiments (e.g., FIGS. 11A-11D). Bone screw 11430 may comprise body 11431 and bone screw head 11440. Bone screw body 11431 may have one or more threads 11432 spanning threaded portion 11433, which may be configured to advance and/or fix bone screw 11430 in a hole in a matrix (e.g., bone). For example, threads 11432 may spirally surround the outer longitudinal circumference of body 11431, tapering to tip 11434. Bone screw body 11430 may have central, longitudinal axis 11435.

Figure 11A:
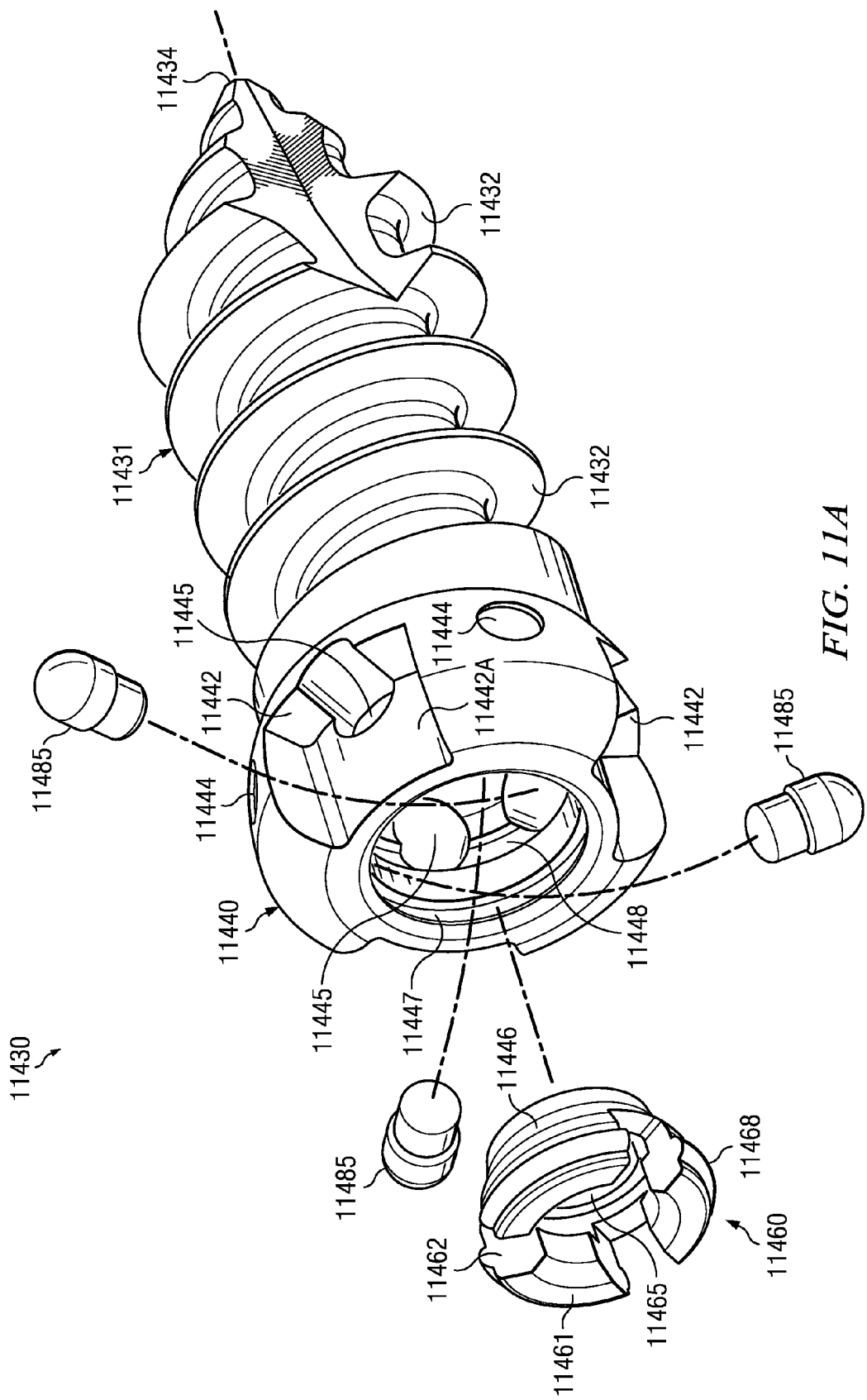
FIG. 11A illustrates an exploded view of a bone screw assembly according to a specific example embodiment of the disclosure.
Figure 11B:
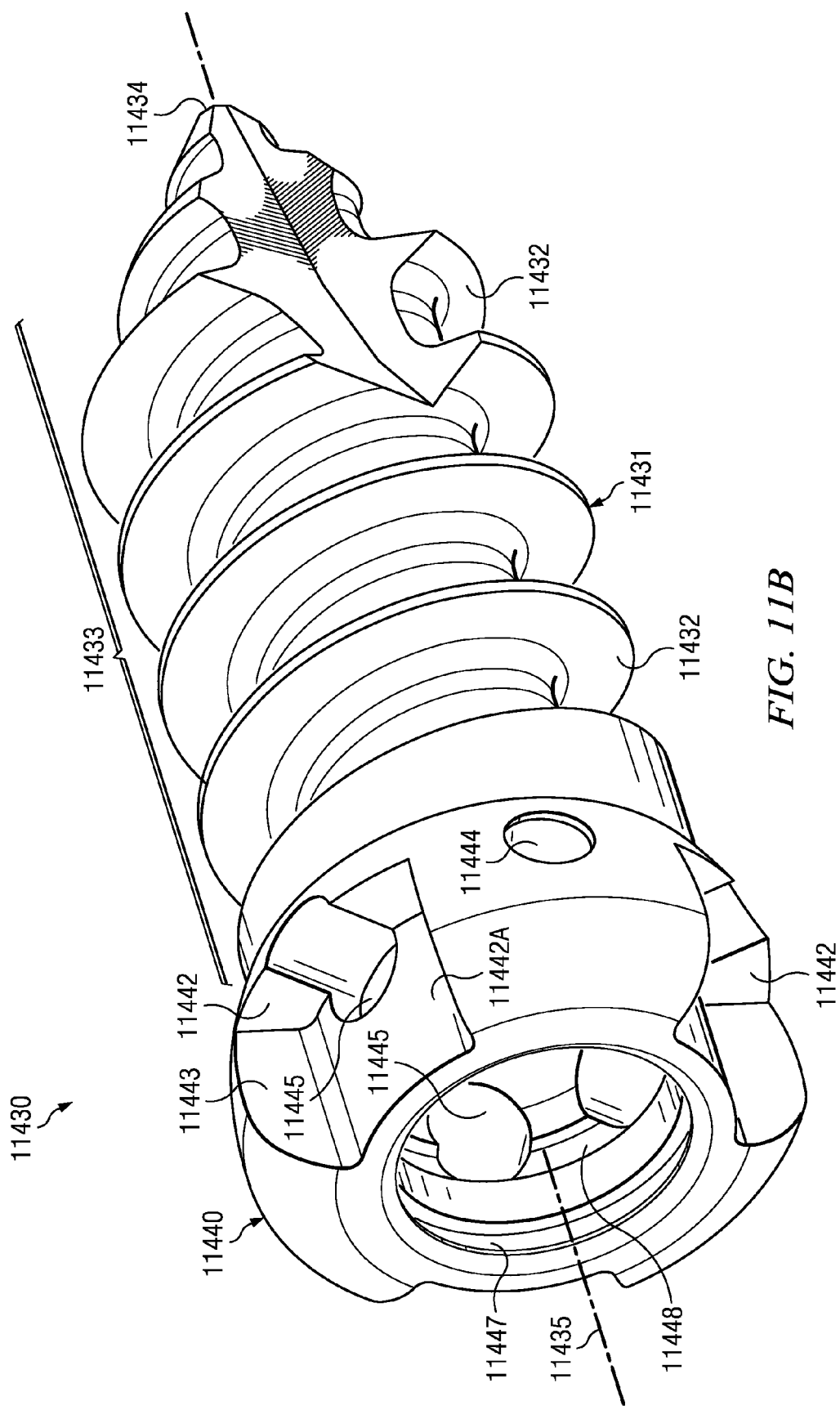
FIG. 11B illustrates a perspective view of a bone screw according to a specific example embodiment of the disclosure.
Figure 11C:
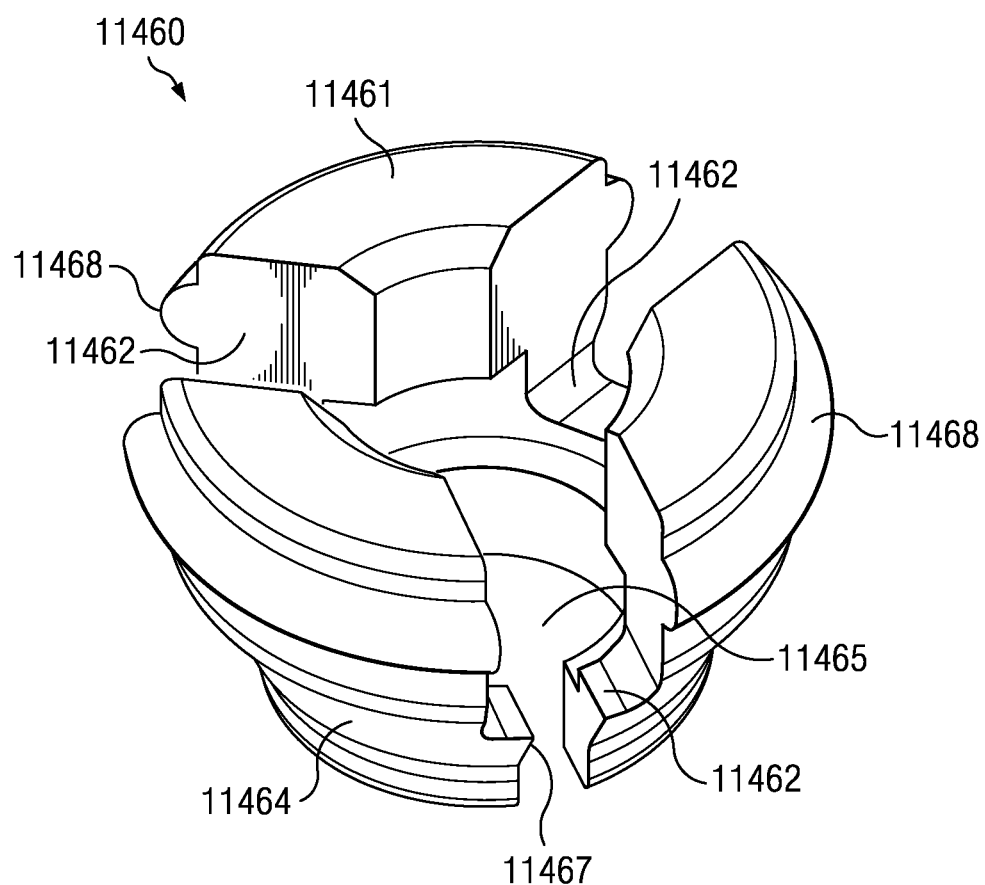
FIG. 11C illustrates a perspective view of a bone screw cam according to a specific example embodiment of the disclosure.

Bone screw head 11440 may comprise notch 11442, torque surface 11443, through holes 11444, through holes 11445, stowed circumferential recess 11447, and deployed circumferential recess 11448. Notch 11442 may be configured to rotate about an axis parallel to and/or rotate in a plane generally perpendicular to longitudinal axis 11435 of bone screw 11430. Each notch 11442 may be bounded by inner notch wall 11442A and, thus, only partially span the radial thickness of body 11441, in contrast to through holes 12444 and 12445, which may span the full radial thickness of body 11441. Notches 11442 may be configured to receive a mated installation tool (e.g., a cylinder with axially protruding circumferential pins dimensioned to engage notches 5242 and/or surfaces 5243). Upon application of a force (e.g., torque) to torque surface 11443, bone screw 11430 may rotate about central longitudinal axis 11435 and, optionally, propel tip 11434 into a matrix (e.g., bone). Stowed circumferential recess 11447, and deployed circumferential recess 11448 may lie in a plane generally perpendicular to longitudinal axis 11435 of bone screw 11430 and/or generally parallel to the rotational plane of notch 11442. Deployed circumferential recess 11448 may be positioned closer to tip 11434 and/or more distant from the apex of bone screw 11430 than stowed circumferential recess 11447. Holes 11444 may receive bone screw pins 11485 (e.g., from their interior faces as illustrated in FIG. 11A). Each hole 11444 and/or each hole 11445 may independently have a longitudinal axis that is perpendicular to center, longitudinal axis 11435 of bone screw 11430. Each hole 11444 may independently have a diameter that is uniform along its full length. In some embodiments, each hole 11444 may independently have a narrowing at or near the end more distal to center, longitudinal axis 11435 of bone screw 11430. Holes 11444 and 11445 may be distributed at regular intervals, as shown, or irregular intervals around the circumference of bone screw head 11440. Bone screw 11430 may be a single piece or two or more conjoined parts according to some embodiments.

Bone screw race 11460 may comprise body 11461, notches 11462, each with surfaces 11463, cam surface 11464, central aperture 11465, central aperture inner surface 11466, slot 11467, and/or nub 11468. Body 11461 may itself define and/or comprise central aperture 11465 and/or may taper at one end. In some embodiments, race 11460 may be solid and lack central aperture 11465. Race 11460 may be generally circular (e.g., annular) with a diameter greater than it's thickness.

Each notch 11462 may span the radial thickness of body 11461 and/or only a portion of the longitudinal thickness of body 11461. Two or more notches 11462—may be positioned on the same face of race 11460 as one another and/or opposite of cam surface 11464. Slot 11467 may span both the radial and longitudinal thickness of body 11461 (e.g., defining a gap in an otherwise annular structure). Slot 11467 may permit (e.g., independently or in cooperation with the resiliency of race 11460 and/or bone screw head 11440) race 11460 to be radially compressed (e.g., temporarily). This may facilitate movement of race 11460 between stowed positions and deployed positions and/or installation of race 11460 in bone screw 11430. Slot 11467 may be contiguous with (as shown) or separate from a notch 11462. Race 11460 may fit (e.g., slidably fit) within a cavity in bone screw head 11440 (e.g., at or near the apex of bone screw 11430). For example, race 11460 may fit within bone screw head 11430 such that it may slide (e.g., reversibly) along longitudinal axis 11435 of bone screw 11430. Race 11460 may be positioned within bone screw head 11440 such that nub 11468 engages stowed circumferential recess 11447 (stowed position) or deployed circumferential recess 11448 (deployed position). As shown, race 11460 may be positioned such that it is flush with bone screw head 11440 (its surface farthest from tip 11434 is level with the surface of bone screw head 11440 that is farthest from tip 11434) in a stowed position. When moved to a deployed position, race 11460 is depressed into bone screw head 11440. Alternatively, race 11460 may be positioned such it is above bone screw head 11440 in a stowed position. When moved to a deployed position, race 11460 then becomes flush with bone screw head 11440. Cam surface 11464 may independently contact one or more bone screw pins 11485.

Bone screw pin 11485 may have a generally cylindrical shape and/or comprise proximal end 11486, ridge 11487, and distal end 11488. Proximal end 11486 may be flat or domed. Distal end 11488 may be flat or domed. Proximal end 11486 may be positioned more proximal to central axis 11435 than distal end 11488. Ridge 11467 may engage stop 11449 (e.g., when pin 11485 is in a deployed position.

FIGS. 12A-12F illustrate perspective, plan, and section views of bone screw assembly 12420 with bone screw pins 12485 in a stowed position (FIGS. 12A, 12C, and 12E) and a deployed position (FIGS. 12B, 12D, and 12F). As shown, each bone screw pin 12485 in an undeployed (or stowed) position may (a) occupy a hole 12444, (b) engage a deep recess 12453 such that its outer edge is substantially flush with the outer surface of head 12440, and/or (c) have little or no opportunity for contact with plate 12410 (FIGS. 12A, 12C, and 12E). Each bone screw pin 12485 in a deployed position may (a) partially occupy a hole 12444, (b) engage a shallow recess 12454 such it that protrudes from hole 12444 beyond the outer surface of head 12440, and/or (c) has sufficient exposure to contact plate 12410 (FIGS. 12B, 12D, and 12F).

In use, each bone screw pin 12485 may be deployed upon application of a force generally along and/or parallel to central axis 12435 and directed toward tip 12434. Race 12460 may slide (e.g., snap) from a stowed position more distant from tip 12434 to a deployed position closer to tip 12434 in which nub 12468 moves from engagement with stowed circumferential recess 12447 to engagement with deployed circumferential recess 12448. Such movement may slide cam surface 12464 across proximal end 12486 and displace (e.g., cam) bone screw pins 12485 radially outwardly from a stowed position to a deployed position. A tool (not pictured) may be inserted into notches 124124 and used to drive race 12460 towards tip 12435. This may continue until nub 12468 engages recess 12448; at which point pins 12485 come to rest in a deployed position (FIG. 12D). If present, recess 12447 may permit screw assembly 12420 to "lock" into an undeployed position (e.g., due to recess 12447's contour and/or the resiliency of the material of which screw assembly 12420 is constructed). If present, recess 12448 may permit screw assembly 12420 to "lock" into a deployed position (e.g., due to recess 12448's contour and/or the resiliency of the material of which screw assembly 12420 is constructed). If desired, bone screw assembly 12420 may be removed by unlocking race 12450 (e.g., by inserting a tool into the center of the race, engaging the tool with an undercut in the center bore of the race, and pulling the race up to the undeployed position) and backing out (e.g., counter-rotating) bone screw 12430.

As will be understood by those skilled in the art who have the benefit of the instant disclosure, other equivalent or alternative locking mechanisms for a screw (e.g., a bone screw) and associated devices, systems, and methods can be envisioned without departing from the description contained herein. Accordingly, the manner of carrying out the disclosure as shown and described is to be construed as illustrative only.

Persons skilled in the art may make various changes in the shape, size, number, and/or arrangement of parts without departing from the scope of the instant disclosure. For example, the position and number of through holes 12, through hole recesses 13, mounts 16, apertures 17, bone screw assemblies 20, threads 32, notches 42, recesses 44, holes 45, recesses 47*m* recesses 48, stops 49, grooves 52, recesses 53, recesses 54, notches 62, surfaces 164, nubs 68, threads 69, notches 72, prongs 174, ball bearings 80, and/or pins 85 may be varied. In some embodiments, bone screw assemblies 20 may be interchangeable. Interchangeability may allow selection of the locking mechanism to be custom adjusted. In addition, the size of a device and/or system may be scaled up (e.g., to be used for adult subjects) or down (e.g., to be used for juvenile subjects) to suit the needs and/or desires of a practitioner. Each disclosed method and method step may be performed in association with any other disclosed method or method step and in any order according to some embodiments. Where the verb "may" appears, it is intended to convey an optional and/or permissive condition, but its use is not intended to suggest any lack of operability unless otherwise indicated. Persons skilled in the art may make various changes in methods of preparing and using a composition, device, and/or system of the disclosure. For example, a system, device, and/or method may be prepared and or used as appropriate for animal and/or human use (e.g., with regard to sanitary, infectivity, safety, toxicity, biometric, and other considerations).

All or a portion of a device and/or system for locking a fastener (e.g., a bone screw) may be configured and arranged to be disposable, serviceable, interchangeable, and/or replaceable. These equivalents and alternatives along with obvious changes and modifications are intended to be included within the scope of the present disclosure. Accordingly, the foregoing disclosure is intended to be illustrative, but not limiting, of the scope of the disclosure as illustrated by the appended claims.

What is claimed is:
1. A lockable bone plate assembly, comprising:
a bone plate including a through hole having a recess, and
a bone screw assembly including
   a bone screw,
   a deployable protrusion having a stowed position at least partially within the bone screw and a deployed position at least partially protruding from the bone screw, the deployable protrusion being operable to engage the recess of the bone plate, and
a protrusion driver in mechanical communication with the deployable protrusion and operable to drive the deployable protrusion from the stowed position to the deployed position, a contacting surface between the protrusion driver and the deployable protrusion having a first radial distance in the stowed position and a second radial distance different from the first radial distance in the deployed position, wherein
the protrusion driver includes a cam, and
a profile of an outer circumference of the cam varies radially in a cross-section taken transverse to a rotational axis of the cam.

2. A lockable bone plate assembly according to claim 1, wherein the protrusion driver is operable to move the deployable protrusion radially outwardly from the stowed position to the deployed position.

3. A lockable bone plate assembly according to claim 1, wherein the protrusion driver has a deployed position corresponding to the deployed position of the deployable protrusion.

4. A lockable bone plate assembly according to claim 3, wherein the protrusion driver is operable to lock in the deployed position.

5. A lockable bone plate assembly according to claim 3, wherein
the bone screw includes a first surface feature, and
the protrusion driver includes a second surface feature operable to engage the first surface feature and to lock the protrusion driver in its deployed position.

6. A lockable bone plate assembly according to claim 1, wherein
the bone screw includes a central, longitudinal axis and a bone screw head having at least one notch, and
each of the bone screw and the bone screw head includes a torque surface operable to receive a torque and translate the torque to rotation of the bone screw about the central, longitudinal axis.

7. A lockable bone plate assembly according to claim 1, wherein the bone screw has a central longitudinal axis and includes:
a bone screw body having threads that taper to a tip; and
a bone screw head fixed to the bone screw body on an end opposite to the tip.

8. A lockable bone plate assembly, comprising
a bone plate including a through hole having a recess, and
a bone screw assembly including
a bone screw,
a deployable protrusion having a stowed position at least partially within the bone screw and a deployed position at least partially protruding from the bone screw, the deployable protrusion being operable to engage the recess of the bone plate, and
a protrusion driver in mechanical communication with the deployable protrusion and operable to drive the deployable protrusion from the stowed position to the deployed position, a contacting surface between the protrusion driver and the deployable protrusion having a first radial distance in the stowed position and a second radial distance different from the first radial distance in the deployed position, wherein
the bone screw has a central longitudinal axis and includes:
a bone screw body having threads that taper to a tip; and
a bone screw head fixed to the bone screw body on an end opposite to the tip, and
the bone screw head includes an annular groove encircling a notch.

9. A lockable bone plate assembly, the lockable bone plate assembly comprising:
a bone plate comprising at least one through hole, the at least one through hole having at least one bone plate hole circumferential recess, and
a bone screw assembly comprising, (a) a bone screw, (b) at least one deployable protrusion having a stowed position substantially within the bone screw and a deployed position at least partially protruding from the bone screw and engaged with the at least one bone plate hole circumferential recess, and (c) a protrusion driver in mechanical communication with the deployable protrusion and operable to drive the deployable protrusion from the stowed position to the deployed position, wherein the vertical position of the bone screw assembly relative to the bone plate is locked when the deployable protrusion is in the deployed position, wherein
the bone screw has a central longitudinal axis and comprises:
a bone screw body comprising threads that taper to a tip; and
a bone screw head fixed to the bone screw body on the end opposite the tip, the bone screw head comprising at least one notch,
the bone screw head further comprises an annular groove encircling the at least one notch, and
the bone screw assembly further comprises:
an annular bone screw cam positioned in the annular groove and comprising on its outer circumferential surface at least one axial groove, at least one axial deep recess, and at least one axial shallow recess between the axial groove and the axial deep recess; and
an annular bone screw cap comprising a first surface comprising at least one bone screw cap notch and second surface opposing the first facing the annular bone screw cam and comprising at least one prong, wherein
the at least one deep recess is configured to engage the deployable protrusion in its stowed position,
the at least one shallow recess is configured to engage the deployable protrusion in its deployed position, and
the at least one axial groove is in mechanical communication with the at least one prong to produce tandem rotation of the annular bone screw cam and annular bone screw cap about the central, longitudinal axis.

10. A lockable bone plate assembly according to claim 9, wherein the annular bone screw cap further comprises at least one circumferential notch comprising a torque surface, the torque surface configured to receive a torque and translate the torque to rotation of the bone screw cap about the central, longitudinal axis.

11. A lockable bone plate assembly, comprising
a bone plate including a through hole having a recess, and
a bone screw assembly including
a bone screw,
a deployable protrusion having a stowed position at least partially within the bone screw and a deployed position at least partially protruding from the bone screw, the deployable protrusion being operable to engage the recess of the bone plate, and
a protrusion driver in mechanical communication with the deployable protrusion and operable to drive the deployable protrusion from the stowed position to the deployed position, a contacting surface between the protrusion driver and the deployable protrusion having a first radial distance in the stowed position and a second radial distance different from the first radial distance in the deployed position, wherein the bone screw has a central longitudinal axis and includes:
 a bone screw body having threads that taper to a tip; and
 a bone screw head fixed to the bone screw body on an end opposite to the tip,
the bone screw head includes a cavity having a cavity inner surface, and
the cavity inner surface includes a stowed recess and a deployed recess, the deployed recess being closer to the tip than the stowed recess.

12. A lockable bone plate assembly, the lockable bone plate assembly comprising:
 a bone plate comprising at least one through hole, the at least one through hole having at least one bone plate hole circumferential recess, and
 a bone screw assembly comprising, (a) a bone screw, (b) at least one deployable protrusion having a stowed position substantially within the bone screw and a deployed position at least partially protruding from the bone screw and engaged with the at least one bone plate hole circumferential recess, and (c) a protrusion driver in mechanical communication with the deployable protrusion and operable to drive the deployable protrusion from the stowed position to the deployed position, wherein the vertical position of the bone screw assembly relative to the bone plate is locked when the deployable protrusion is in the deployed position, wherein
 the bone screw has a central longitudinal axis and comprises:
  a bone screw body comprising threads that taper to a tip; and
 a bone screw head fixed to the bone screw body on the end opposite the tip, the bone screw head comprising at least one notch, and
 the bone screw assembly further comprises:
  an annular bone screw race in the central cavity having a stowed position and a deployed position, the annular bone screw race comprising
   a first end,
   an outer circumferential surface comprising at least one circumferential nub and at least one cam surface, and
   a second end opposite the first end,
  wherein the nub engages the stowed circumferential recess in the stowed position of the race and the nub engages the deployed circumferential recess in the deployed position of the race.

13. A lockable bone plate assembly according to claim 12, wherein the deployable protrusion comprises a bone screw pin having a generally cylindrical shape and comprising a proximal end in mechanical communication with the at least one cam surface of the annular bone screw race and a distal end engageable with the at least one bone plate hole circumferential recess.

14. A lockable bone plate assembly according to claim 13, wherein the annular bone screw race further comprises a slot spanning its radial and longitudinal thickness.

15. A lockable bone plate assembly according to claim 14, wherein the annular bone screw race comprises a central aperture comprising a central aperture surface, the central aperture surface comprising threads.

16. A lockable bone plate assembly according to claim 14, wherein the first end of the cam comprise at least one cam notch and the slot is distinct from each at least one cam notch.

17. A lockable bone plate assembly according to claim 14, wherein the slot is contiguous with at least one cam notch.

18. A method of vertebral fixation, comprising:
 contacting at least a portion of a spine of a subject with a lockable bone plate assembly, the lockable bone plate assembly including:
  a bone plate including a through hole having a recess, and
  a bone screw assembly including
   a bone screw,
   a deployable protrusion having a stowed position at least partially within the bone screw and a deployed position at least partially protruding from the bone screw, the deployable protrusion being operable to engage the recess of the bone plate, and
   a protrusion driver in mechanical communication with the deployable protrusion and operable to drive the deployable protrusion from the stowed position to the deployed position, a contacting surface between the protrusion driver and the deployable protrusion having a first radial distance in the stowed position and a second radial distance different from the first radial distance in the deployed position, wherein
   the protrusion driver includes a cam, and
   a profile of an outer circumference of the cam varies radially in a cross-section taken transverse to a rotational axis of the cam.

19. A method of vertebral fixation according to claim 18, wherein the at least a portion of the spine of the subject includes at least a portion of the subject's cervical spine.

20. A bone screw assembly, comprising:
 a bone screw;
 a deployable protrusion having a stowed position at least partially within the bone screw and a deployed position at least partially protruding from the bone screw; and
 a protrusion driver in mechanical communication with the deployable protrusion and operable to drive the deployable protrusion from the stowed position to the deployed position, a contacting surface between the protrusion driver and the deployable protrusion having a first radial distance in the stowed position and a second radial distance different from the first radial distance in the deployed position, wherein
 the protrusion driver includes a cam, and
 a profile of an outer circumference of the cam varies radially in a cross-section taken transverse to a rotational axis of the cam.

* * * * *